(12) United States Patent
Zhuang et al.

(10) Patent No.: US 11,401,317 B2
(45) Date of Patent: Aug. 2, 2022

(54) HUMAN-CD123-TARGETING CHIMERIC RECEPTOR LIGAND AND APPLICATION THEREOF

(71) Applicant: Nanjing Legend Biotech Co., Ltd., Nanjing (CN)

(72) Inventors: Qiuchuan Zhuang, Nanjing (CN); Xiaohu Fan, Edmonton (CA); Lei Yang, Huainan (CN); Pingyan Wang, Fengyang (CN)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 555 days.

(21) Appl. No.: 16/329,739

(22) PCT Filed: Aug. 31, 2017

(86) PCT No.: PCT/CN2017/099941
§ 371 (c)(1),
(2) Date: Feb. 28, 2019

(87) PCT Pub. No.: WO2018/041220
PCT Pub. Date: Mar. 8, 2018

(65) Prior Publication Data
US 2019/0225668 A1 Jul. 25, 2019

(30) Foreign Application Priority Data
Aug. 31, 2016 (CN) .......................... 201610795955.X

(51) Int. Cl.
| | | |
|---|---|---|
| *C07K 14/54* | (2006.01) | |
| *C07K 14/705* | (2006.01) | |
| *A61K 35/17* | (2015.01) | |
| *C12N 15/62* | (2006.01) | |
| *A61P 35/02* | (2006.01) | |
| *C12N 5/10* | (2006.01) | |
| *A61P 35/00* | (2006.01) | |
| *C07K 19/00* | (2006.01) | |
| *C12N 15/867* | (2006.01) | |
| *C12N 15/86* | (2006.01) | |

(52) U.S. Cl.
CPC ........ *C07K 14/70517* (2013.01); *A61K 35/17* (2013.01); *A61P 35/00* (2018.01); *A61P 35/02* (2018.01); *C07K 19/00* (2013.01); *C12N 5/10* (2013.01); *C12N 15/62* (2013.01); *C12N 15/86* (2013.01); *C12N 15/867* (2013.01)

(58) Field of Classification Search
CPC .. C07K 4/7051; C07K 14/54; C07K 14/5403; A61P 35/00; A61K 35/17; A61K 39/0011
See application file for complete search history.

(56) References Cited

U.S. PATENT DOCUMENTS

| | | | |
|---|---|---|---|
| 9,657,105 B2 * | 5/2017 | Forman | ............... C07K 14/7051 |
| 2008/0138313 A1 * | 6/2008 | Frankel | ................ A61K 38/164 |
| | | | 424/85.2 |

* cited by examiner

*Primary Examiner* — Karen Cochrane Carlson
(74) *Attorney, Agent, or Firm* — Klarquist Sparkman, LLP

(57) ABSTRACT

The present invention relates to a human CD123-targeting chimeric receptor ligand, comprising an IL-3 molecule-based CD123 binding domain, a transmembrane region, and an intracellular signaling domain. The present invention provides a T cell modified by the human CD123-targeting chimeric receptor ligand and capable of specifically binding with CD123 on tumor cell surfaces, thereby having specific cytotoxicity on tumor cells. The present invention further relates to an application of the human CD123-targeting chimeric receptor ligand and an immune effector cell thereof in preparing an anti-tumor immunotherapy drug.

23 Claims, 7 Drawing Sheets
Specification includes a Sequence Listing.

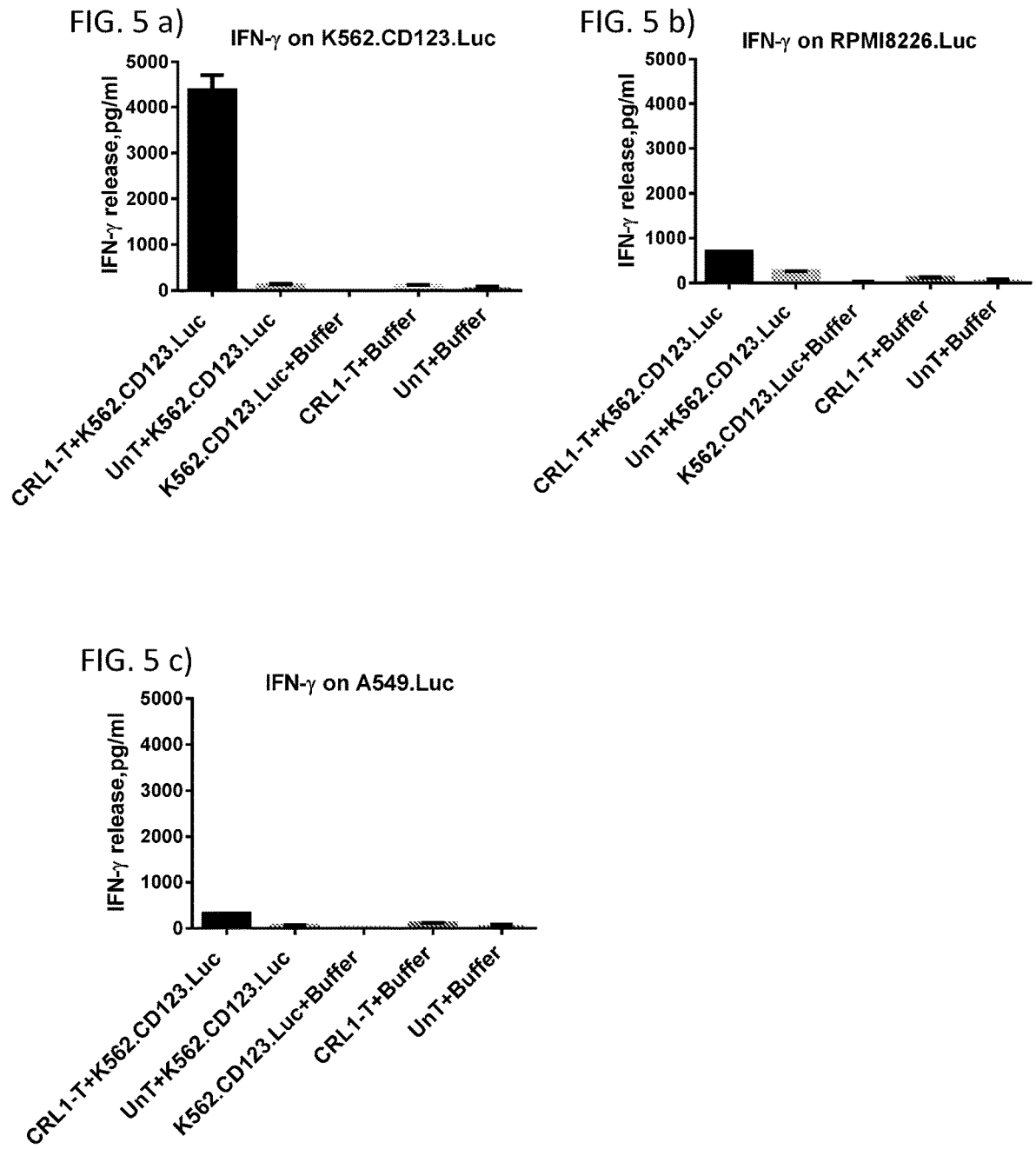

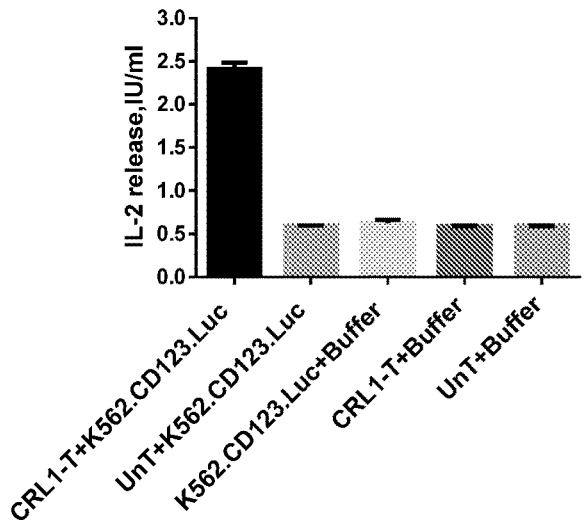
FIG. 6 a) IL-2 on K562.CD123.Luc
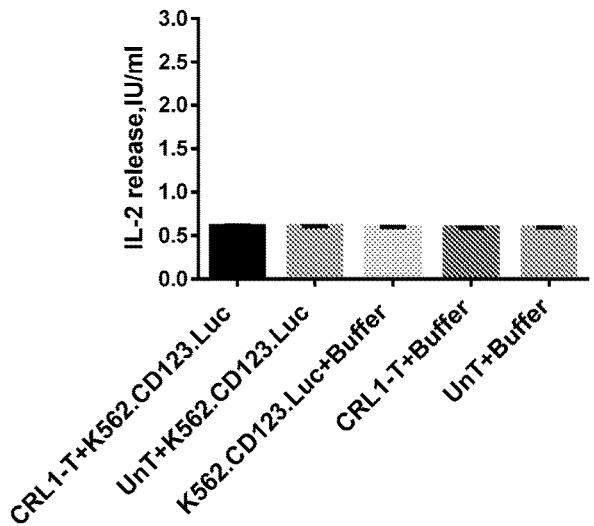
FIG. 6 b) IL-2 on RPMI8226.Luc
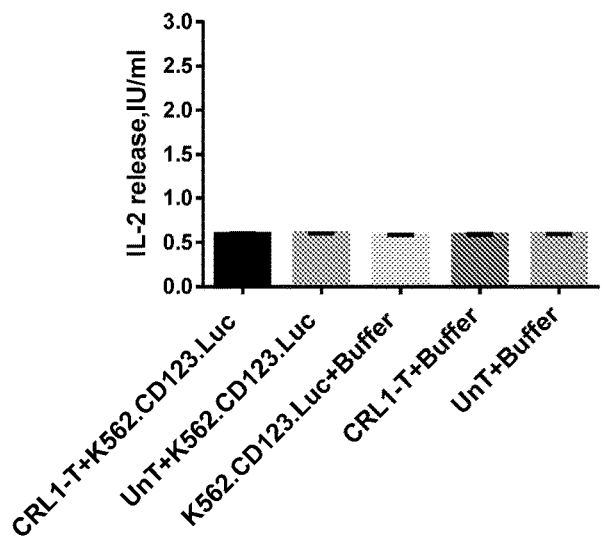
FIG. 6 c) IL-2 on A549.Luc

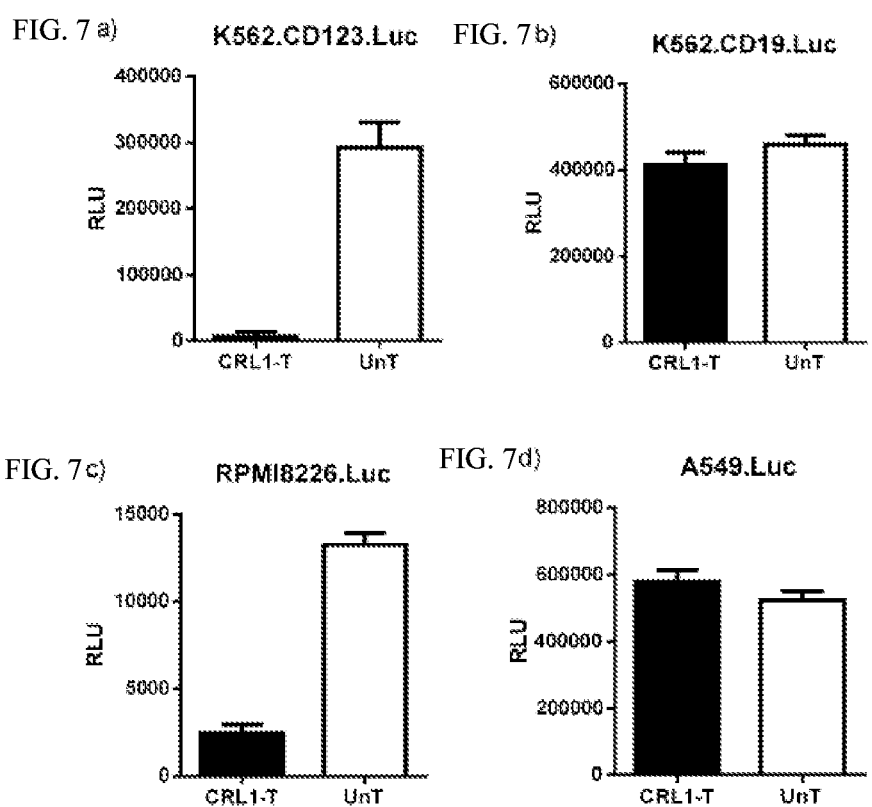

HUMAN-CD123-TARGETING CHIMERIC RECEPTOR LIGAND AND APPLICATION THEREOF

CROSS REFERENCE TO RELATED APPLICATIONS

This is the U.S. National Stage of International Application No. PCT/CN2017/099941, filed Aug. 31, 2017, which was published in English under PCT Article 21(2), which in turn claims the benefit of Chinese Application No. 201610795955.X, filed Aug. 31, 2016, which are incorporated herein by reference in their entirety.

FIELD OF THE INVENTION

The present invention belongs to the field of biomedical or biopharmaceutical technologies, and relates to a human CD123-targeting chimeric receptor ligand and an application thereof.

DESCRIPTION OF THE RELATED ART

CD123, i.e., human interleukin-3 receptor a chain (Interleukin-3 receptor subunit alpha, IL-3Rα), has a full length of 378 amino acids (NP_002174.1), wherein a signal peptide comprises 18 amino acids (1-18), an extracellular region comprises 287 amino acids (19-305), a transmembrane region comprises 20 amino acids (306-325), and an intracellular region comprises 53 amino acids (326-378). Research over the past 20 years has shown that CD123 is overexpressed in many blood tumors, including acute myeloid leukemia (AML), acute B-cell lymphocytic leukemia (B-ALLs), hairy cell leukemia, and blastic plasmacytoid dendritic cell tumor (BPDCN). Muñoz L et al. detected 64 acute leukemia patients and found that 43 out of 45 AML patients thereof were CD123 positive, 2 M7 AML patients were CD123 negative, 13 B-cell acute leukemia patients thereof were all CD123 positive, while 6 T-cell acute leukemia patients were all CD123 negative (Haematologica. 2001, December; 86 (12): 1261-9). Xueqiang Ji et al. reported that bone marrow lymphocytes from healthy children had negative CD123 expression, bone marrow lymphocytes from 65 out of 91 child B-ALL patients had positive CD123 expression (a positive rate of 71.43%), and the expression levels were negatively correlated with the maturity of leukemia cells (Journal of Jiangsu University: Medical Science Edition, 2012). A Ehninger et al. also reported that 79% (232/298) of AML patients had cells expressing CD123 molecules. These reports have all shown that CD123 is a good blood disease therapeutic target for AML (Blood Cancer Journal, 2014).

Human interleukin-3 (IL-3) is a native ligand of CD123. Human IL-3 gene is located on human chromosome V (5q23-31) and has a molecular weight of approximately 15-17 kDa. IL-3 molecule is not conserved in evolution, and there is only 29% amino acid homology between human IL-3 molecules and mouse IL-3 molecules. IL-3 and its receptor CD123 (IL-3R) have a very high affinity (Kd=0.1~1 nM).

DT388IL-3 is a fusion protein of IL-3 molecule and diphtheria toxin. In in vitro studies, DT388IL-3 exhibits a good affinity with CD123 (Kd=3 nM) and good CD123 antigen selective cytotoxicity ($IC_{50}$=5~10 pM) (Protein Eng. 2000, August; 13 (8): 575-81), and no significant cytotoxicity on normal cells (Cancer Res. 2002, Mar. 15; 62 (6): 1730-6). In in vivo experiments with mice, DT388IL-3 significantly increased the survival of mice carrying IL-3 receptor positive AML cells with no significant side effects (Leukemia. 2003 January; 17 (1): 155-9). In the safety assessment of cynomolgus monkeys, DT388IL-3 also showed good safety (Leuk Lymphoma. 2004, August; 45 (8): 1647-56). The good safety of DT388IL-3 also discloses the safety of use of interactions of ligands and receptors between IL-3 and CD123 for treatment of diseases.

Over recent years, Chimeric Antigen Receptor Modified T cell therapy (CAR-T) has achieved encouraging progress in clinical trials of blood disease treatment. Starting from the first case of complete remission of acute B-cell lymphoblastic leukemia in a child (Emily Whitehead) through CD19-targeting CAR-T therapy as reported by the group led by Carl H. June in 2013, the CAR-T cell immunotherapy has entered a stage of rapid development in just a few years. The CTL019 with CD19 as a target that was developed by teams with that of Novartis and the University of Pennsylvania as a representative achieves a rate of complete remission above 90% in children and young adults having relapsed/refractory acute lymphoblastic leukemia (r/r ALL). As of August 2016, the retrieve information from the US Clinical Trials registration website (clinicaltrials.gov) shows that there are 142 registered CAR-T clinical trials worldwide, wherein 71 were registered in the United States and 51 trials were registered in China. Currently, comprehensive research and product development have been performed on CAR-T therapy for diseases like acute myeloid leukemia (AML), multiple myeloma (MM), glioma, colon cancer, prostate cancer, and the like.

Chimeric antigen receptor (CAR) consists of a tumor-associated antigen-binding region or antigen-binding domain, an extracellular hinge region, a transmembrane region, an intracellular signal transduction domain, etc. The CAR antigen-binding domain typically consists of antibodies in different forms. Currently, most of the developed CAR-T immunotherapy have antigen recognition sequences in a form that is based on scFv antibody fragments. For example, the anti-human CD123 murine antibodies used by relevant research teams in the Abramson Cancer Center at the University of Pennsylvania and in the City of Hope, USA include clone32716 and clone26292, wherein clone32716 exhibits better in vitro and in vivo antitumor activities of killing CD123-positive cells than clone26292 does, and can remove CD123-positive tumor cells in the mouse models within two weeks (J Immunother. 2007, September; 30(6): 607-13; US20140271582A1; Blood. 2013; 122(18): 3138-3148). French CELECTIS has also developed a CD123 CAR-T vector, and the CD123 antibody used therein is Klon43 (WO2015193406A1). Clinical trials of CAR-T therapy for AML registered in the US Clinical Trials registration website mainly include NCT02159495 in the City of Hope and NCT02623582 in the Abramson Cancer Center of the University of Pennsylvania. These CAR-T cells and immunotherapies thereof that are designed based on scFv antibodies all may lead to off-target effects that are common to CAR technologies due to possible cross reactivity among the selected antibodies themselves. Therefore, it is necessary to cautiously verify their safety in clinical trials. Since all of the above CD123 CAR-T use murine monoclonal antibodies as CD123 targeting molecules, a potential immunogenicity may exist when they are applied to a human body.

SUMMARY OF THE INVENTION

By following the principle of interaction between ligands and receptors, the present invention provides a human CD123-targeting Chimeric Receptor Ligand (CRL), which is different from the conventional CAR configuration based on antibody scFv fragments, but a brand-new, antibody-independent, and human CD123-targeting structure similar to that of CAR. The human CD123-targeting CRL (CD123 CRL) according to the present invention may comprise a native IL-3 molecule-based CD123-specific binding domain, a hinge region or non-hinge region, a transmembrane region, an intracellular signal transduction domain, etc. The present invention further provides a CRL-modified immune cell, i.e., CD123 CRL-modified T cell (CRL-T). The human CD123-targeting CRL and immune cells thereof according to the present invention have CD123 target specific tumor killing effect and safety that are better than those of conventional scFv antibody-based CD123 CAR-T; the use of the native human IL-3 molecule-based CD123-targeting molecules for immunotherapy does not lead to heterologous immunogenicity; and the present invention is very valuable in clinical treatment of CD123 positive blood diseases and other diseases.

An object of the present invention is to provide a human CD123-targeting chimeric receptor ligand.

Another object of the present invention is to provide a genetically engineered immune effector cell.

Another object of the present invention is to provide an application of the human CD123-targeting chimeric receptor ligand and the immune effector cell thereof.

A further object of the present invention is to provide a method for preparing human CD123-targeting chimeric receptor ligands and immune effector cells thereof.

The objects of the present invention can be achieved by the following technical solution:

a human CD123-targeting chimeric receptor ligand, comprising an IL-3 molecule-based CD123 specific binding domain, transmembrane region and intracellular signaling domain.

In an embodiment of the present invention, the CD123 specific binding domain of the human CD123-targeting chimeric receptor ligand comprises an amino acid sequence shown by SEQ ID NO: 1 or SEQ ID NO: 2 that specifically binds CD123, or an amino acid sequence having 85% to 99%, 90% to 99%, or 95% to 99% identity therewith.

In an embodiment of the present invention, the intracellular signaling domain of the human CD123-targeting chimeric receptor ligand comprises a signaling domain and/or co-stimulatory signaling domain.

The signaling domain of the intracellular signaling domain can be selected from CD3 zeta, CD3 gamma, CD3 delta, CD3 epsilon, common FcR gamma (FCER1G), FcR beta (Fc Epsilon R1b), CD79a, CD79b, Fc gamma RIIa, DAP10, and DAP12 molecules, preferably CD3 zeta molecules.

The co-stimulatory signaling domain of the intracellular signaling domain can be selected from intracellular domains of the following signal molecules: CD27, CD28, 4-1BB, OX40, CD30, CD40, CD2, lymphocyte function-associated antigen-1 (LFA-1), LIGHT, NKG2C, B7-H3, PD-1, ICOS, CDS, ICAM-1, GITR, BAFFR, HVEM (LIGHTR), SLAMF7, CD7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244,2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELJPLG (CD162), LTBR, LAT, GADS, SLP-76, PAG/Cbp, NKp44, NKp30, NKp46, NKG2D, and CD83-specific binding ligands or any combination thereof.

The intracellular signaling domain is more preferably selected from intracellular signaling domains of the following molecules: CD3 zeta, 4-1BB and/or CD28.

The transmembrane domain of the human CD123-targeting chimeric receptor ligand can be selected from the TCRα, TCRβ, TCRγ, CD3ζ, CD3ε, CD5, CD9, CD16, CD22, CD27, CD28, CD33, CD37, CD45, CD64, CD80, CD86, CD134, CD154, CD152, CD4, CD8α, CD28, PD1 and 4-1BB transmembrane regions, preferably CD8a, CD28, and/or 4-1BB transmembrane regions.

In an embodiment of the present invention, the human CD123-targeting chimeric receptor ligand comprises a protein secretion related signal peptide sequence that can be selected from CD8α signal peptide, GM-CSFRα signal peptide, CD4 signal peptide, or IL-3 signal peptide, preferably IL-3 signal peptide.

The human CD123-targeting chimeric receptor ligand can comprise a hinge region structure or does not comprise a hinge region structure, and the hinge region can be selected from CD8a and CD28 molecules.

The extracellular and transmembrane regions of the human CD123-targeting chimeric receptor ligand may comprise a Linker structure or do not comprise a Linker structure.

The human CD123-targeting chimeric receptor ligand according to the present invention may comprise two or more repeating CD123 chimeric receptor ligands in serial connection, a plurality of IL-3 molecule based CD123 binding domains in mutual serial connection, or a combination of multivalent target-specific chimeric receptor ligands formed by an IL-3 molecule based CD123 binding domain and an antibody-based antigen binding domain in serial connection, wherein repeating units can be connected by one or more Linker structures therebetween.

In an embodiment of the present invention, the human CD123-targeting chimeric receptor ligand is characterized in that the encoded amino acid sequence is shown by SEQ ID NO: 14 to SEQ ID NO: 19, or is a modified amino acid sequence having 85% to 99%, 90% to 99%, or 95% to 99% identity therewith.

A nucleic acid molecule is characterized by a nucleotide sequence that encodes the human CD123-targeting chimeric receptor ligand.

In an embodiment of the present invention, the nucleic acid molecule is characterized in that the nucleotide coding sequence is shown by SEQ ID NO: 33 to SEQ ID NO: 38.

A vector is characterized by comprising the nucleic acid sequence that encodes the human CD123-targeting chimeric receptor ligand.

A genetically engineered immune effector cell comprises a gene sequence that encodes the human CD123-targeting chimeric receptor ligand according to the present invention.

The immune effector cell is preferably selected from T-lymphocyte cells, NK cells, and immune cells from culturing and differentiation of hematopoietic stem cells, pluripotent stem cells or embryonic stem cells, more preferably T lymphocytes.

The genetically engineered immune cells are characterized in that the expressed human CD123-targeting chimeric receptor ligand comprises an IL-3 molecule-based CD123 specific binding domain, a transmembrane region, and an intracellular signaling domain.

In an embodiment of the present invention, the genetically engineered immune cells are characterized in that the expressed human CD123-targeting chimeric receptor ligand comprises an amino acid sequence shown by SEQ ID NO: 14, or an amino acid sequence having 85% to 99%, 90% to 99%, or 95% to 99% identity therewith.

In an embodiment of the present invention, the genetically engineered immune cells are characterized in that the expressed human CD123-targeting chimeric receptor ligand comprises an amino acid sequence shown by SEQ ID NO: 15, SEQ ID NO: 16, SEQ ID NO: 17, SEQ ID NO: 18, or SEQ ID NO: 19, or an amino acid sequence having 85% to 99%, 90% to 99%, or 95% to 99% identity therewith.

The present invention provides a method for preparing the above-described human CD123-targeting chimeric receptor ligand and modified immune effector cells thereof.

The present invention relates to a use of the human CD123-targeting chimeric receptor ligand and immune effector cells thereof in the manufacture of a medicament for anti-tumor immunotherapy, preferably a use in the manufacture of a medicament for treating acute myeloid leukemia.

Advantageous Effects

The present invention provides a human CD123-targeting CRL (CD123 CRL), which creatively uses a human IL-3 molecule as an extracellular specific CD123 molecule-targeting binding region, specifically recognizes tumor-associated surface antigen CD123 through ligand/receptor, then transfers recognition signals into cells through intracellular co-stimulatory molecules, activates the killing effect of immune cells, and thus reduces and eliminates tumor cells. At the same time, the present invention provides a human CD123-targeting CRL-modified T cell (CD123 CRL-T), which can specifically bind with CD123 on the surface of tumor cells, thereby having a specific killing effect on tumor cells. Compared with the conventional CD123 CAR-T based on an antibody, such as scFv fragments, CD123 CRL-T exhibits better CD123 target specific tumor killing effect and cytokine release amount, thereby improving specificity and safety of targeted treatment.

BRIEF DESCRIPTION OF THE DRAWINGS

FIG. 1a is a schematic structural diagram of the IL-3 based CD123 chimeric receptor ligand according to the present invention, wherein the structure of the signal peptide part can be selected from IL-3 and CD8α molecules. 4-1BB and/or CD28 signaling molecules are used as examples of the co-stimulatory signaling domain. FIG. 1b is a schematic structural diagram of conventional scFv antibody-based CD123 CAR-T.

As shown in FIG. 4a, the Y-axis shows relatively activity RLU of the remaining luciferase in reaction wells and relative amount of living cells in the corresponding wells when co-culture ends. CAR1-T, CAR2-T, CAR3-T and CRL1-T cells all have good in vitro cytotoxicity against RPMI8226.Luc cells. As shown in FIG. 4b, CAR1-T, CAR2-T, CAR3-T and CRL1-T cells can all release cytokines IFNγ in the presence of RPMI8226.Luc cells. In the absence of RPMI8226.Luc cells, on the other hand, CRL1-T exhibits a lower release amount of IFNγ cytokine than those by CAR1-T, CAR2-T and CAR3-T.

FIGS. 5a-5c illustrate a detection test on cytokine IFN-γ release level of IL-3 molecule based CD123 CRL-T. FIG. 5a illustrates the IFN-γ level released by CRL1-T cells in the presence of K562.CD123.Luc that causes over expression and low expression of CD123 molecules; FIG. 5b illustrates the IFN-γ level released by CRL1-T cells under stimulation by RPMI8226.Luc cells that cause low expression of CD123 molecules; and FIG. 5c illustrates the IFN-γ level released by CRL1-T cells under stimulation by CD123-negative A549.Luc cells.

FIGS. 6a-6c illustrate a detection test on cytokine IL-2 release level of IL-3 molecule based CD123 CRL-T. FIG. 6a illustrates the IL-2 level released by CRL1-T cells in the presence of K562.CD123.Luc that causes over expression and low expression of CD123 molecules; FIG. 6b illustrates the IL-2 level released by CRL1-T cells under stimulation by RPMI8226.Luc cells that cause low expression of CD123 molecules; and FIG. 6c illustrates the IL-2 level released by CRL1-T cells under stimulation by CD123-negative A549.Luc cells.

FIGS. 7a-7d illustrate assessment of functionality and specificity of the IL-3 based CD123 CRL-T. FIG. 7a illustrates that, compared with the negative control UnT cells, CRL1-T has good in vitro cytotoxicity on K562.CD123.Luc cells that cause over expression of CD123; FIG. 7b illustrates that CRL1-T almost has no in vitro cytotoxicity on CD123-negative K562.CD19.Luc cells; FIG. 7c illustrates that CRL1-T cells have good in vitro cytotoxicity on RPMI8226.Luc cell lines that cause low expression of CD123; FIG. 7d illustrates that CRL1-T cells have no in vitro cytotoxicity at all on lung cancer cell line A549.Luc that does not express CD123 molecules.

DETAILED DESCRIPTION OF THE INVENTION

Figure 1:
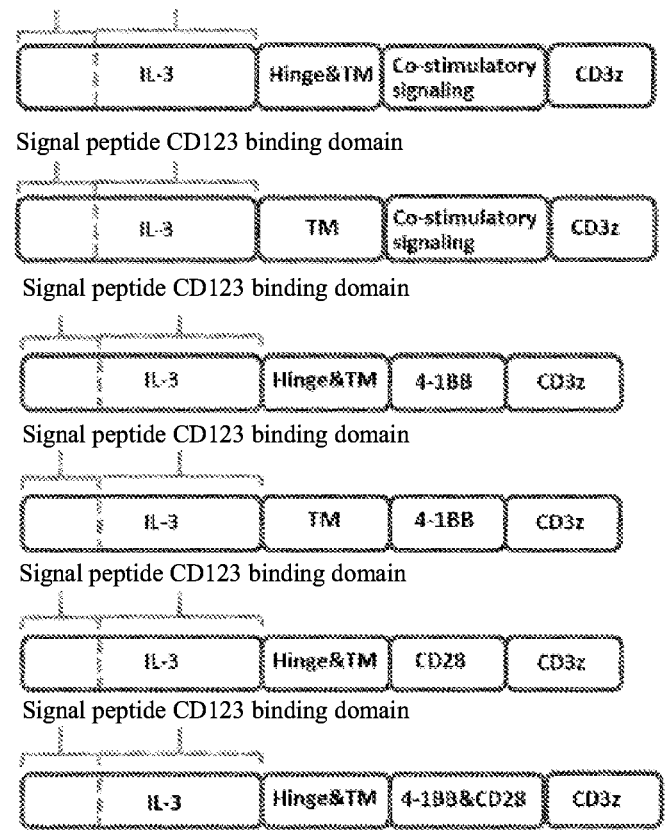
FIGS. 1a and 1b show a schematic structural diagram of a human CD123-targeting chimeric receptor ligand constructed according to the present invention.
Figure 1:
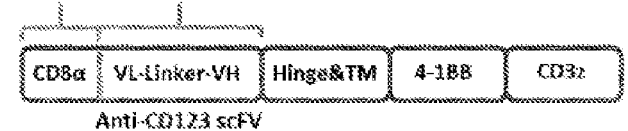
Figure 2:
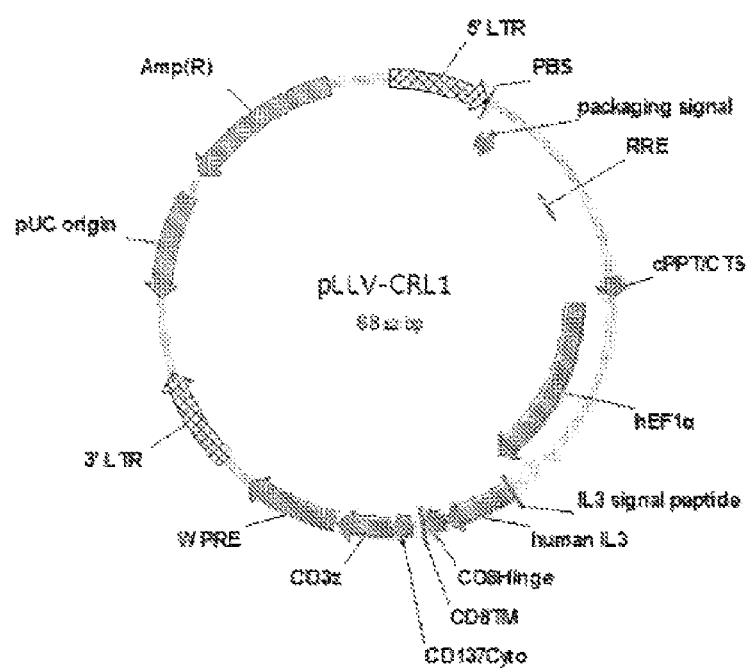
FIG. 2 is a schematic diagram of a human CD123-targeting chimeric receptor ligand vector constructed according to the present invention. The structural diagram of the CD123 CRL vector constructed according to the present invention is illustrated with CRL1 as an example, and the illustrated CRL1 comprises IL-3 extracellular signal peptide, CD123 binding domain, CD8α hinge region (Hinge) and transmembrane region (TM), the 4-1 BB intracellular co-stimulatory domain (Cyto) and CD3z signaling domain.
Figure 3:
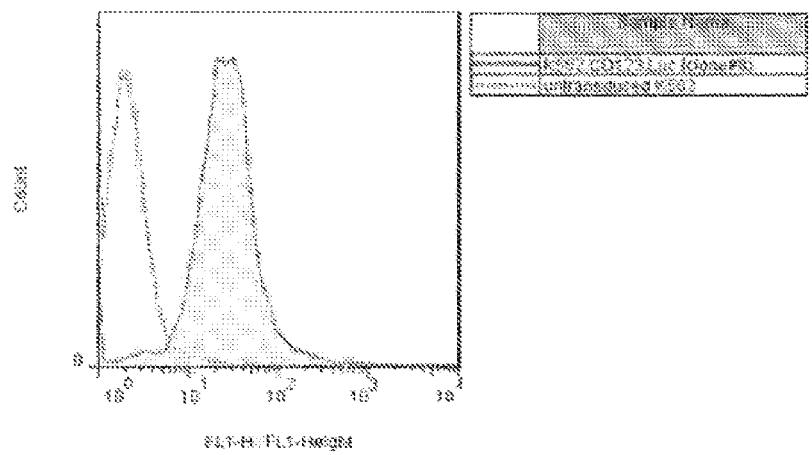
FIG. 3 illustrates verification of K562.CD123.Luc cell lines. CD123 molecules in the constructed clone 8 cell lines have the highest expression level, Luciferase also has a high expression level, and clone 8 is named as K562.CD123.Luc.

The present invention provides a human CD123-targeting chimeric receptor ligand, comprising an IL-3 molecule-based CD123 binding domain, a transmembrane region, and an intracellular signaling domain.

The term used herein, "IL-3 molecule-based CD123 binding domain," refers to a CD123 binding domain from a native human IL-3 amino acid sequence.

The amino acid sequence of native human IL-3 is shown by SEQ ID NO: 40, which contains a total of 152 amino acid residues. The 19 amino acid residues on the N terminal of native human IL-3 molecule are an IL-3 signal peptide, which has an amino acid sequence as shown by SEQ ID NO: 3.

If the signal peptide portion (SEQ ID NO: 3) is removed from the native human IL-3 molecule, the SEQ ID NO: 1 sequence (comprising 133 amino acids) can be obtained. SEQ ID NO: 1 can be used as an IL-3 receptor binding domain (also referred to as CD123 binding domain), which has the ability to specifically bind CD123.

If the 9 amino acids on the C terminal of SEQ ID NO: 1 are removed, SEQ ID NO: 2 (containing 124 amino acids) can be obtained. An IL-3 fragment containing only SEQ ID NO: 2 sequence can also bind CD123, and may be used as an IL-3 receptor binding domain.

The "IL-3 molecule-based CD123 binding domain" used herein has the ability to specifically bind CD123. For example, in an embodiment of the present invention, the IL-3 molecule-based CD123 binding domain may comprise at least 100 contiguous amino acid residues of SEQ ID NO: 1, such as 102, 105, 110, 115, or 120 contiguous amino acid residues.

In a preferred embodiment of the present invention, the IL-3 molecule-based CD123 binding domain may be SEQ ID NO: 1 or SEQ ID NO: 2.

The human CD123-targeting chimeric receptor ligand according to the present invention can comprise one IL-3 molecule-based CD123 binding domain, or can comprise two or more IL-3 molecule-based CD123 binding domains. These CD123 binding domains may or may not be identical. For example, there can be two or more repeating CD123 chimeric receptor ligands in serial connection, a plurality of IL-3 molecule-based CD123 binding domains in mutual serial connection, or a combination of multivalent target-specific chimeric receptor ligands formed by an IL-3 molecule based CD123 binding domain and an antibody-based antigen binding domain in serial connection, wherein repeating units can be connected by one or more Linker structures therebetween.

The term used herein, "Linker" also referred to as the connecting peptide or linker, is a flexible amino acid sequence for connection of two domains. It would be easy for a person skilled in the art to select and prepare a connecting peptide.

The term used herein, "transmembrane region" (TM in short) can be used interchangeably with "transmembrane domain" and refers to a thermodynamically stable protein structure area anchored in the cell membrane. The transmembrane region may be obtained from native proteins and selected from CD8α molecule or CD28 molecule. For example, an amino acid sequence shown by SEQ ID NO: 6 or 7.

The term used herein, "intracellular signaling domain," refers to a protein structure area capable of conducting cell effector function signals and directing cells to perform a specific function. The intracellular signaling domain may comprise a signaling domain and/or co-stimulatory signaling domain.

The term used herein, "identity" of amino acid sequences, can be used interchangeably with "sameness" and refers to a degree of similarity between the amino acid sequences determined by sequence comparison software, such as BLAST. Methods and software for comparison of amino acid sequences are well known to a person skilled in the art.

A modified amino acid sequences can be obtained by performing substitution, deletion and/or addition of one or several (e.g. 1-15, e.g. 2, 3, 5, 8, 10, or 12) amino acid residues on a known amino acid sequence.

For example, the CD123 binding domain shown by SEQ ID NO: 1 in the present invention is modified through a conventional protein engineering technique (e.g. conservative amino acid substitution and the like) to obtain a variant sequence having at least 85% (e.g., 85% to 99%, 90% to 99%, or 95% to 99%) sequence identity with SEQ ID NO: 1, and having substantially the same CD123 binding capacity (e.g., retaining at least 80%, such as at least 85%, 90% or even 95% binding capacity)

The term used herein, "scFv" or "scFv antibody," refers to a single chain antibody (scFv), which is formed by connecting a heavy chain variable region and a light chain variable region of the antibody via a short peptide having 15 to 20 amino acids.

Preferably, the human CD123-targeting chimeric receptor ligand according to the present invention can further comprise an extracellular signal peptide structure, for example, IL-3 signal peptide or CD8α signal peptide.

The present invention is designed through combining the native human IL-3 molecule and chimeric receptor binding ligand structures, such as co-stimulatory factor. The present invention will be further described below with reference to specific examples.

Example 1 Construction of K562 Cell Line K562.CD123.Luc that Expresses CD123

K562 cells hardly express CD123. First, the present invention obtains a nucleotide sequence that encodes the human CD123 molecule through gene synthesis, and GenScript Biotech Corp. in Nanjing provided the gene synthesis service. Under the action of T4 ligase, the synthesized CD123 nucleotide sequence is connected, at 20° C. overnight, to a pLVX-Puro (Clontech, Catalog #632164) lentiviral vector that has been subjected to digestion of BamH1 and XbaI restriction sites in advance. The ligation product is transformed into DH5α competent cells and spread onto a bacterial plate. A plurality of clone patches is picked for plasmid extraction (Qiagen Endofree Mega kit). Upon restriction enzyme digestion, sequencing and comparison, sequencing match, the successfully constructed vector is named pLVX-CD123-Puro.

The extracted pLVX-CD123-Puro expression plasmid and pCMV-ΔR-8.74 and pMD2.G helper plasmids are mixed according to a certain ratio, and 293FT cells are co-transfected. At 96 h after transfection, the virus-containing cell culture supernatant is collected and centrifuged for 5 min at 4° C. and 3000 rpm. After filtration through a 0.45 μm filter, the supernatant is subjected to high speed centrifugation for 120 min at 4° C. and 25000 rpm. The supernatant is discarded, a concentrated virus solution is obtained through resuspension and dissolution, and the concentrated virus solution is stored at −80° C. for later use. A lentiviral vector carrying the firefly luciferase/Luciferase reporter gene is prepared also by the same method.

The K562 cell line is purchased from ATCC (Catalog #CCL-243), and is cultured conventionally using 90% IMDM (Life technology, Catalog #A10491-01)+10% FBS (Life technology, Catalog #10099-141)+1% penicillin/streptomycin (Life technology, Catalog #15140-122). The constructed lentiviral vector carrying CD123 genes and the lentiviral vector carrying Firefly luciferase/Luciferase reporter gene are added to the culture supernatant of K562 cells for co-transduction into K562 cells. At 24 h after transduction, Puromycin with a final concentration of 10 μg/ml is added, the culture is replaced once every three days and Puromycin having the same concentration is added, and monoclonal screening is further performed to get some monoclonal cells.

CD123 expression identification is performed using flow cytometry on monoclonal cells obtained above. K562 cells that are not transduced with the CD123 gene are used as negative control. The cell suspension having a cell number of 5×10⁵ is pipetted to a 15 ml centrifuge tube for centrifugation at room temperature and 300 g, and the supernatant is discarded after 10 min DPBS is used for resuspension and washing once, and then it is re-suspended in 200 µl DPBS. 2 µl anti-CD123-FITC antibody (Miltenyi, Catalog #130-098-886) is further added for incubation at room temperature for 45 min 1 ml DPBS is added, centrifugation is performed at room temperature and 300 g, and the supernatant is discarded after 10 min 1 ml DPBS is further added, centrifugation is performed at room temperature and 300 g, and the supernatant is discarded after 10 min Lastly, 200 µl DPBS-resuspended cells are added, and FITC signals are detected on a FACScalibur flow cytometer (BD Inc.). Luciferase assay is performed using the One-Glo Luciferase assay kit (Promega, Catalog #E6110): the cell density of each clone is adjusted to 2000 cells/20 µl, which is then added to a 384-well microwell plate, 20 µl One-Glo Luciferase assay reagent is added to each well, centrifugation is performed at room temperature and 300 g, and after 1 min, the plate is left undisturbed for 10 min Subsequently, chemiluminescence signals are detected on a PHERAstar microplate reader (purchased from BMG).

By the above procedure, 9 stable cell lines with high expression of CD123 molecules and Luciferase are obtained. As listed in Table 1, detection results of the positive rate of CD123 expression and Luciferase relative enzyme activity (RLU, relative light unit) of the constructed cell lines show that the constructed cell lines with different clone numbers express different levels of CD123 molecules and different levels of Luciferase, respectively. Clone 8 has the highest level of CD123 molecule expression, 92.9% of the cells are CD123 positive cells, while K562 cells with no transduction has a CD123 positive rate only at 3.31%. At the same time, clone 8 also has a relatively high level of Luciferase, and its signal value is 659 times of that of the negative K562 cells control with no transduction (relative enzyme activity 761623/1156). In summary, clone 8 is a good cell line, and clone 8 is named K562.CD123.Luc and used as a tool cell in subsequent experiments.

TABLE 1

Construction of K562 cell line K562.CD123.Luc that expresses CD123

| Clone Numbers | CD123 positive rate | Relative enzyme activities of Luciferase (RLU) |
|---|---|---|
| clone 1 | 3.27% | 27052 |
| clone 2 | 56.20% | 371620 |
| clone 3 | 70.20% | 944192 |
| clone 4 | 80.80% | 360250 |
| clone 5 | 70.90% | 230302 |
| clone 6 | 73.30% | 273153 |
| clone 7 | 74.10% | 211465 |
| clone 8 | 92.90% | 761623 |
| clone 9 | 85.20% | 56267 |
| K562 with no transduction | 3.31% | 1156 |

Example 2 Construction of a Human IL-3 Molecule-Based Human CD123-Targeting Chimeric Receptor Ligand According to the present invention, codon optimization of a nucleotide sequence of a human IL-3 molecule is performed, so as to optimize the expression in human cells. The codon optimization is implemented using the Optimum-Gene™ codon optimization technique of GenScript Biotech Corp. in Nanjing. The IL-3 nucleotide sequence after the codon optimization is shown by SEQ ID NO: 39, the amino acid sequence encoded thereby is shown by SEQ ID NO: 40, and the IL-3 molecule expressed by the gene comprises IL-3 signal peptide and IL-3 receptor binding domain.

According to the present invention, the CD123 CRL fusion gene fragment is designed in the following order of encoding genes: an extracellular signal peptide, an IL-3-based CD123 binding domain, a hinge region (Hinge), a transmembrane region (TM), an intracellular co-stimulatory signaling domain, and an intracellular signaling domain. GenScript Biotech Corp. in Nanjing provides technical services for synthesis of the fusion gene. The basic structure of the IL-3-based human CD123-targeting chimeric receptor ligand according to the present invention is shown in Table 2, comprising a chimeric receptor ligand structure shown by CRL1 to CRL6, and the corresponding amino acid sequences of the chimeric receptor ligand thereof are shown by SEQ ID NO: 14 to SEQ ID NO: 19, respectively.

According to the present invention, conventional CARs are also designed as experimental controls, and the fusion gene is directly synthesized using a gene synthesis technique in an order of CD8α signal peptide, anti-CD123 scFv, CD8α hinge region (Hinge), CD8α transmembrane region (TM), 4-1BB intracellular co-stimulatory signaling domain, and CD3ζ intracellular signaling domain, respectively, as the CAR1, CAR2 and CAR3 structures shown in Table 2.

The major structural components and sequence of CD123 CRL designed by the present invention is as follows:

CD123 binding domain: the CD123 binding domain comprises at least 100 contiguous amino acid sequences in the amino acid sequence shown by SEQ ID NO: 1. In an embodiment of the present invention, the IL-3 molecule-based CD123 binding domain comprises the amino acid sequence shown by SEQ ID NO: 1 or SEQ ID NO: 2. The nucleotide encoding sequence thereof is shown by SEQ ID NO: 20 or SEQ ID NO: 21.

Extracellular signal peptide: it may be selected from IL-3 signal peptide or CD8α signal peptide. The amino acid sequence of the IL-3 signal peptide is shown by SEQ ID NO: 3, and the nucleotide encoding sequence thereof is shown by SEQ ID NO: 22; the amino acid sequence of the CD8α signal peptide is shown by SEQ ID NO: 4, and the nucleotide encoding sequence thereof is shown by SEQ ID NO: 23.

Hinge region: it may be selected from hinge regions of a variety of molecules, the CD8α hinge region is selected for CRL1, the amino acid sequence thereof is shown by SEQ ID NO: 5, and the nucleotide encoding sequence thereof is shown by SEQ ID NO: 24.

Transmembrane domain: it may be selected from CD8α transmembrane region or CD28 transmembrane region. The amino acid sequence of the CD8α transmembrane region is shown by SEQ ID NO: 6, and the nucleotide encoding sequence thereof is shown by SEQ ID NO: 25; the amino acid sequence of the CD28 transmembrane region is shown by SEQ ID NO: 7, and the nucleotide encoding sequence thereof is shown by SEQ ID NO: 26.

Intracellular signaling domain: the amino acid sequence of CD3 zeta is shown by SEQ ID NO: 8, and the nucleotide encoding sequence thereof is shown by SEQ ID NO: 27.

Intracellular co-stimulatory signaling domain: selected from 4-1BB signaling molecule or CD28 signaling molecule. The amino acid sequence of the 4-1BB signaling molecule s is shown by SEQ ID NO: 9, and the nucleotide encoding sequence thereof is shown by SEQ ID NO: 28. The amino acid sequence of the CD28 signaling molecule is shown by SEQ ID NO: 10, and the nucleotide encoding sequence thereof is shown by SEQ ID NO: 29.

TABLE 2

Explanation of main CRL and CAR composite structures according to the present invention

| No. | Source of CD123 binding domain | Other components | Amino acid sequence |
|---|---|---|---|
| CAR1 | 32716 scFv | CD8α signal peptide, 4-1BB co-stimulatory domain, and CD3 signaling domain | SEQ ID NO: 11 |
| CAR2 | 26292 scFv | CD8α signal peptide, 4-1BB co-stimulatory domain, and CD3 signaling domain | SEQ ID NO: 12 |
| CAR3 | Klon43 scFv | CD8α signal peptide, 4-1BB co-stimulatory domain, and CD3 signaling domain | SEQ ID NO: 13 |
| CRL1 | IL-3 | IL-3 signal peptide, 4-1BB co-stimulatory domain, and CD3 signaling domain | SEQ ID NO: 14 |
| CRL2 | IL-3 | IL-3 signal peptide, CD28 co-stimulatory domain, and CD3 signaling domain | SEQ ID NO: 15 |
| CRL3 | IL-3 | IL-3 signal peptide, CD28 + 4-1BB co-stimulatory domain, and CD3 signaling domain | SEQ ID NO: 16 |
| CRL4 | IL-3 | CD8α signal peptide, 4-1BB co-stimulatory domain, and CD3 signaling domain | SEQ ID NO: 17 |
| CRL5 | IL-3 | CD8α signal peptide, CD28 co-stimulatory domain, and CD3 signaling domain | SEQ ID NO: 18 |
| CRL6 | IL-3 | CD8α signal peptide, CD28 + 4-1BB co-stimulatory domain, and CD3 signaling domain | SEQ ID NO: 19 |

Example 3 Preparation of CD123 Specific Chimeric Receptor Ligand Modified T Cells (I) Construction of CD123 Chimeric Receptor Ligand Lentiviral Vector According to the present invention, the pLVX-Puro vector purchased from Clontech is subjected to a digestion reaction with ClaI and EcoRI restriction enzymes to knock out the CMV promoter, and the human EF1α promoter (GenBank: J04617.1) is cloned into the digested vector to obtain a pLVX-hEF1α vector. The CD123 CRL fusion gene sequence from gene synthesis is cloned to an expression plasmid pLVX-hEF1α to form a recombinant CRL expression plasmid. The recombinant CRL expression plasmid (pLLV-CRL) is extracted and mixed with pCMV-AR-8.74 and pMD2.G helper plasmids according to a certain ratio, and 293FT cells are co-transfected. At 96 h after transfection, the virus-containing cell culture supernatant is collected and centrifuged for 5 min at 4° C. and 3000 rpm. After filtration through a 0.45 μm filter, the supernatant is subjected to high speed centrifugation for 120 min at 4° C. and 25000 rpm. The supernatant is discarded, a concentrated virus solution is obtained through resuspension and dissolution, and the concentrated virus solution is stored at −80° C. for later use.

Recombinant CRL lentivirus vectors obtained using the above method are named as pLLV-CRL1, pLLV-CRL2, pLLV-CRL3, . . . , pLLV-CRL6, respectively.

As a control in the experiments, scFv antibody sequences of the above-described clone 32716, clone 26292, and Klon43 are synthesized and cloned into the lentiviral vector according to the present invention, which are named as pLLV-CAR1, pLLV-CAR2 and pLLV-CAR3, respectively.

The construction of the above vectors employs conventional molecular biology techniques, i.e., digestion, ligation, transformation, and cloning identification techniques, which can be easily grasped and operated by those of ordinary skills in the art.

(II) Preparation of T Lymphocytes 50 mL of fresh peripheral blood is taken from volunteers, and peripheral blood mononuclear cells (PBMC) are isolated using lymphocyte isolation liquid and density gradient centrifugation method. A Pan T Cell Isolation Kit (Miltenyi Biotech) is used to label the cells with magnetic beads, and T lymphocytes are isolated and purified. CD3/CD28 magnetic beads are further used to perform T lymphocyte activation and proliferation on the purified T cells.

(III) Lentiviral Transduction of T Lymphocytes

Activated T lymphocytes are collected and resuspended in RPMI1640 medium. Lentivirus is used infect $1\times10^6$ activated T lymphocytes, the cell suspension is added to 6-well plates, which are placed in an incubator at 37° C. and 5% $CO_2$ overnight. On the second day, centrifugation is performed again, and the culture is replaced with a fresh medium. Fresh medium is added every 2 days to continue expanding the culture.

(IV) Fluorescence Quantitative Real-Time qPCR Detection of CRL Transduction Efficiency The prepared CRL-T and CAR-T cells are collected through centrifugation, the cells are washed 3 times with DPBS, and then genomic DNA is prepared using a human genome extraction kit Gentra Puregene Cell Kit (purchased from Qiagen). The $OD_{260\,nm}$ and $OD_{280\,nm}$ absorbance of the prepared DNA is detected using NanoDrop2000 (Thermo Scientific), and the concentration is calculated. 50 μl reaction system is configured according to the instructions for the kit SYBR Green Realtime PCR Master mix plus (purchased from Toyobo), and then the gene copy number is detected on a fluorescence quantitative PCR instrument (ABI #7300). The qPCR detection uses a plasmid containing a fragment of interest that has been accurately quantified as a positive control, and a standard curve is plotted. Straight lines are plotted according to the CT values of qPCR at various copy number concentrations and corresponding copy numbers to fit the standard curve. Relative copy numbers are calculated for other detection samples according to the fitting equation of the standard curve.

For detection of chimeric receptor ligand expressed by CRL-T cells in the present invention, CAR expressed by CAR-T cells is used as a positive control, and non-transduced T-lymphocytes (UnT) are used as a blank control.

Detection results of copy numbers of CRL and CAR integration are shown in Table 3. The results show that CRL1 gene integration is detected in the CRL1-T cell genome, and its copy number ($2.34\times10^5$ copies/ng genomic DNA) is equivalent to the copy number of CAR gene transduced in CAR-T cells ($3.1\times10^4$ to $2.77\times10^5$ copies/ng genomic DNA), and the UnT detection value is very low (16 copies/ng genomic DNA) for the blank control, which is the detection background.

TABLE 3 qPCR detection of CRL cell transduction efficiency

| Group | Ct detection value 1 | Ct detection value 1 | Ct detection average value | Copy number/ng genomic DNA |
| --- | --- | --- | --- | --- |
| CAR1 | 18.05 | 19.88 | 18.96 | 3.10E+04 |
| CAR2 | 18.26 | 18.32 | 18.29 | 4.77E+04 |
| CAR3 | 15.47 | 15.62 | 15.54 | 2.77E+05 |
| CRL1 | 15.73 | 15.89 | 15.81 | 2.34E+05 |
| UnT | 30.77 | 30.77 | 30.77 | 16 |

Example 4 Study on In Vitro Active Functions of CD123 Molecule-Targeting Ligand Chimeric Receptor Ligands RPMI8226 cells express a certain level of CD123 receptors (proteinatlas.org/ENSG0000018 5291-IL-3RA/tissue), and it has been reported that CD123 molecule-targeting CAR-T has good in vitro cytotoxicity on RPMI8226 cells (WO2015193406A1). According to the present invention, a RPMI8226 cell line that stably expresses Luciferase is constructed (RPMI8226.Luc), and Example 1 can be referenced to for the construction method. According to the present invention, RPMI8226.Luc cells are used as model cells for the study on in vitro functions of CRL-T cells, and CAR1, CAR2, CAR3 modified T cells are used as controls, which are named as CAR1-T, CAR2-T, and CAR3-T, respectively.

Figure 4:
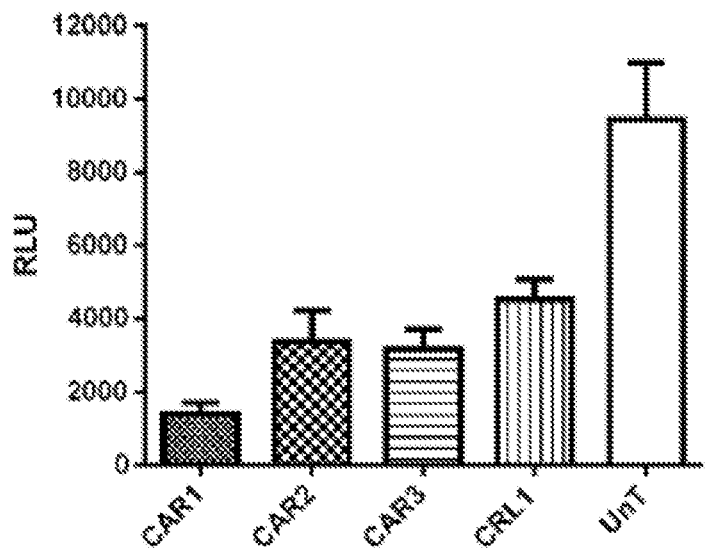
FIGS. 4a and 4b illustrate a study on in vitro active functions of the CD123-targeting chimeric receptor ligand.
Figure 4:
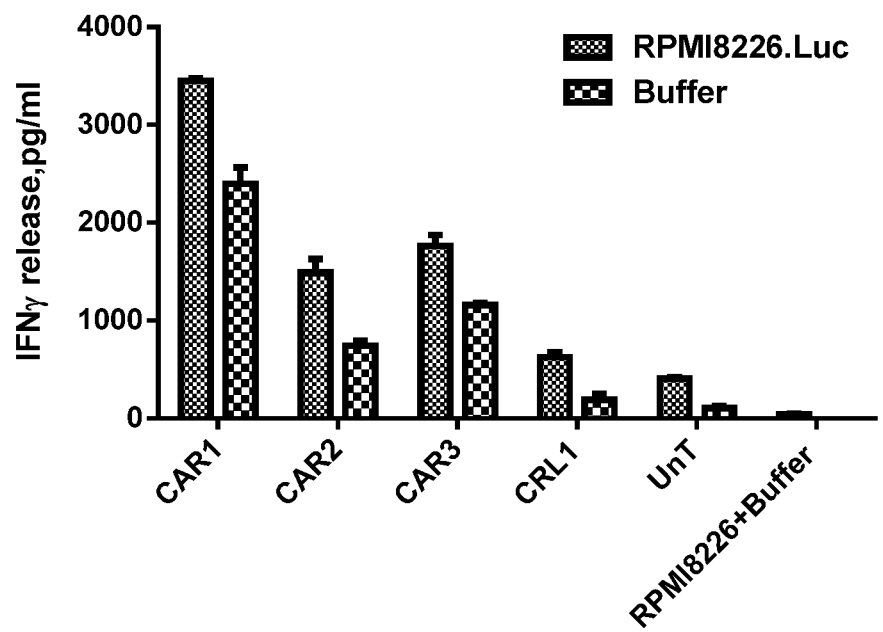

CRL-T cells, CAR-T cells, and UnT cells are co-cultured overnight with target cells, respectively, at a ratio of 20:1 at 37° C. and 5% $CO_2$. After the co-culture is ended, they are subjected to centrifugation and then the ONE-Glo™ Luciferase Assay reagent is added. A PHERAStar Plus is used to detect RLU reading and evaluate in vitro cytotoxicity. As shown in FIG. 4a, the Y-axis shows the remaining relative luciferase activity (RLU, relative light unit) in reaction wells after the end of co-culture. If the displayed luciferase RLU value is high, it indicates that there are many target cells remaining in the reaction wells that are not killed and the cytotoxicity in the wells is low; conversely, if the displayed luciferase RLU value is low, it indicates that there are not many target cells remaining in the reaction wells that are not killed and the cytotoxicity in the wells is high.

As shown in FIG. 4a, CAR1-T, CAR2-T, CAR3-T, and CRL1-T cells all have good in vitro cytotoxic activities on RPMI8226.Luc cells, wherein the relative Luciferase signal value of the remaining viable cells in the CAR1-T treated group is 1413±152, the relative Luciferase signal value of the remaining viable cells in the CAR2-T treated group is 3883±423 RLU, the relative Luciferase signal value of the remaining viable cells in the CAR3-T treated group is 3184±262, and the relative Luciferase signal value of the remaining viable cells in the CRL1-T treated group is 4531±276, which show good killing activities relative to the relative Luciferase signal value of the remaining viable cells in the UnT treated group that is 9442±1553.

The release of cytokines ($\gamma$-interferon/IFN-$\gamma$ and interleukin-2/IL-2) under antigen-specific stimulation is an indicator to evaluate the in vitro activity and application safety of CAR-T. A good CAR-T vector can release the above cytokines in the presence of a target antigen, while the release level is relatively low in the absence of a target antigen. The detection results in FIG. 4b show that CAR1-T, CAR2-T, CARS-T, and CRL1-T cells can all release the cytokine IFN$\gamma$ in the presence of RPMI8226.Luc cells. Among them, it is shown that CAR1-T has better in vitro cytotoxicity than that of CAR2-T, CARS-T, and CRL1-T (FIG. 4a), but CAR1-T can release, in the absence of RPMI8226.Luc target cells, the cytokine IFN$\gamma$ at a level that is significantly higher than that of the cytokine IFN$\gamma$ released by CAR2-T, CARS-T, and CRL1-T, indicating a relatively high non-specificity. In the absence of RPMI8226.Luc target cells, CRL1-T shows a release amount of the cytokine IFN$\gamma$ that is lower than that of CAR1-T, CAR2-T, and CARS-T, and at the same time, CRL1-T has a cytotoxicity on RPMI8226.Luc that is equivalent to that of CAR2-T and CARS-T, indicating a relatively good in vitro effectiveness and safety.

Example 5 Release of Tumor Cytokine by IL-3 Molecule-Based CD123 CRL-T Cells

According to the present invention, the CRL1 vector is preferably selected for T cell modification, and stimulation tests by cytokines IFN-$\gamma$ and IL-2 are performed on CD123-positive tumor cells. In the present invention, CRL-T cells and different target cells are co-cultured overnight at certain ratios, 37° C. and 5% $CO_2$. After the co-culture is ended, the test microplates are centrifuged at 200 g for 5 min, and then a part of the supernatant is carefully taken out for detection of IFN-$\gamma$ and IL-2 secretion levels in the supernatant using a kit for real-time fluorescence resolution technique (HTRF, Cisbio #64IL2PEB).

As shown in FIG. 5a, in the presence of K562.CD123.Luc that overexpresses CD123 molecules, CRL1-T cells release a high level of IFN-$\gamma$ (4383±236.1 pg/ml), whereas negative T cells (UnT) have a very low level of release (108.6±23.97 pg/ml) that is close to the baseline (29.78±37.52 pg/ml); when K562.CD123.Luc is missing, CRL1-T cells release a very low level of background IFN-$\gamma$ (109.3±10.41 pg/ml) that is close to the baseline (29.78±37.52 pg/ml). As stimulated by RPMI8226.Luc cells having a low expression of CD123 molecules, CRL1-T cells can also release a higher level of IFN-$\gamma$ (697.4±0.00 pg/ml, 261.6±3.1 pg/ml) than UnT cells do (FIG. 5b). As stimulated by CD123-negative A549.Luc cells, CRL1-T cells are similar to the UnT cell control, both of which release a low level of IFN-$\gamma$ (315±0.00 pg/ml, 58.54±11.53 pg/ml) (FIG. 5c).

As shown in FIG. 6a, in the presence of K562.CD123.Luc that overexpresses CD123 molecules, CRL1-T cells release a high level of IL-2 (2.41±0.06 IU/ml), whereas UnT cells have a very low level of release (0.60±0.00 IU/ml) that is close to the baseline (0.59±0.00 IU/ml); when there is no stimulation by K562.CD123.Luc cells, CRL1-T cells release a very low level of IL-2 (0.59±0.00 IU/ml) that is the same as the baseline (0.59±0.00 IU/ml). As stimulated by RPMI8226.Luc cells having a low expression of CD123 molecules, CRL1-T cells also release a relatively low level of IL-2 (0.61±0.00 IU/ml) (FIG. 6b). As stimulated by CD123-negative A549.Luc cells, CRL1-T cells are similar to the UnT cell negative control, both of which release a very low level of IL-2 (0.60±0.00 IU/ml, 0.60±0.00 IU/ml) (FIG. 6c).

Example 6 Evaluation of Functions and Specificity of IL-3 Molecule-Based CD123 CRL-T Cells CRL-T cells, CAR-T cells, and UnT cells are co-cultured overnight with target cells, respectively, at a ratio of 20:1 at 37° C. and 5% $CO_2$. After the co-culture is ended, they are subjected to centrifugation and then the ONE-Glo™ Luciferase Assay reagent is added. A PHERAStar Plus is used to detect RLU reading and evaluate in vitro cytotoxicity. As shown in FIG. 7, just like in Example 4, the Y-axis shows the remaining relative luciferase activity (RLU) in reaction wells after the end of co-culture, which corresponds to the relative number of viable cells in the wells. If the displayed luciferase RLU value is high, it indicates that there are many target cells remaining in the reaction wells that are not killed and the cytotoxicity in the wells is low; conversely, if the displayed luciferase RLU value is low, it indicates that there are not many target cells remaining in the reaction wells that are not killed and the cytotoxicity in the wells is high.

As shown in FIG. 7, CRL1-T shows a good in vitro cytotoxic effect on K562.CD123.Luc cells that overexpress CD123 with 97.5% of K562.CD123.Luc cells killed by CRL1-T and without being killed by the negative control UnT; the Luciferase relative light value of the remaining cells in the CRL1 killing group is 7307±3639, whereas the Luciferase relative light value of the remaining cells in the negative control UnT cell killing group is 292420±19102 (FIG. 7a). CRL1-T has almost no in vitro cytotoxicity on CD123-negative K562.CD19.Luc cells; the Luciferase relative light value of the remaining cells in the CRL1 killing group is 411629±14399, whereas the Luciferase relative light value of the remaining cells in the negative control UnT cell killing group is 458030±11222 (FIG. 7b). FIG. 7a and FIG. 7b show that the cytotoxicity of CRL1-T has strict target specificity.

According to the present invention, in vitro killing experiments are further performed on the multiple myeloma cell line RPMI8226.Luc having a low expression of CD123 molecules and the lung cancer cell line A549.Luc that does not express CD123 molecules. As shown in FIG. 7c, just like in Example 4, CRL1-T cells have a good in vitro cytotoxic effect on the RPMI8226.Luc cell line: the Luciferase relative light value of the remaining cells in the CRL1 killing group is 2467±239.6, whereas the Luciferase relative light value of the remaining cells in the negative control UnT cell killing group is 13248±331.3; while CRL1-T has no in vitro cytotoxicity at all on the lung cancer cell line A549.Luc that does not express CD123 molecules: the Luciferase relative light value of the remaining cells in the CRL1 killing group is 577341±17365, whereas the Luciferase relative light value of the remaining cells in the negative control UnT cell killing group is 522895±14198 (FIG. 7d). FIG. 7c and FIG. 7d further show that the cytotoxicity of CRL1-T cells has strict target specificity and safety.

Experimental methods that are not described in detail in the present application document are all conventional techniques in the art and can be implemented according to documents or technical means prior to the filing date.

SEQUENCE LISTING

```
The Sequence Listing is submit-
ted as an ASCII text file named "Sequence.txt,"
created on Apr. 3, 2019, ~64 KB, which is incorporated by reference herein.
Amino acid sequence of IL-3 receptor binding domain: SEQ ID NO: 1 1-133aa
APMTQTTPLKTSWVNCSNMIDEIITHLKQPPLPLLDFNNLNGEDQDILMENNLRRPNLEAFNRAVK
SLQNASAIESILKNLLPCLPLATAAPTRHPIHIKDGDWNEFRRKLTFYLKTLENAQAQQTTLSLAIF Amino acid sequence of IL-3 receptor binding domain: SEQ ID NO: 2 1-124aa
APMTQTTPLKTSWVNCSNMIDEIITHLKQPPLPLLDFNNLNGEDQDILMENNLRRPNLEAFNRAVK
SLQNASAIESILKNLLPCLPLATAAPTRHPIHIKDGDWNEFRRKLTFYLKTLENAQAQ Amino acid sequence of IL-3 signal peptide: SEQ ID NO: 3
MSRLPVLLLLQLLVRPGLQ Amino acid sequence of CD8α signal peptide: SEQ ID NO: 4
MALPVTALLLPLALLLHAARP Amino acid sequence of CD8α hinge region: SEQ ID NO: 5
TTTPAPRPPTPAPTIASQPLSLRPEACRPAAGGAVHTRGLDFACD Amino acid sequence of CD8α transmembrane region: SEQ ID NO: 6
IYIWAPLAGTCGVLLLSLVITLYC Amino acid sequence of CD28 transmembrane region: SEQ ID NO: 7
FWVLVVVGGVLACYSLLVTVAFIIFWV Amino acid sequence of CD3z: SEQ ID NO: 8
RVKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR Amino acid sequence of 4-1BB intracellular region: SEQ ID NO: 9
KRGRKKLLYIFKQPFMRPVQTTQLEDGCSCRFPEELEGGCEL Amino acid sequence of CD28 intracellular region: SEQ ID NO: 10
RSKRSRLLHSDYMNMTPRRPGPTRKHYQPYAPPRDFAAYRS
```

```
                           SEQUENCE LISTING

Amino acid sequence of CAR1: SEQ ID NO: 11
MALPVTALLLPLALLLHAARPDIVLTQSPASLAVSLGQRATISCRASESVDNYGNTFMHWYQQKP
GQPPKLLIYRASNLESGIPARFSGSGSRTDFTLTINPVEADDVATYYCQQSNEDPPTFGAGTKLELK
GGGGSGGGGSSGGGSQIQLVQSGPELICKPGETVKISCKASGYIFTNYGMNWVKQAPGKSFKWMG
WINTYTGESTYSADFKGRFAFSLETSASTAYLHINDLKNEDTATYFCARSGGYDPMDYWGQGTSV
TVSSTSTTTPAPRPPTPAPTIASQPLSLRPEACRPAAGGAVHTRGLDFACDIYIWAPLAGTCGVLLLS
LVITLYCKRGRKKLLYIFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKMAEAYSEIGMKGER
RRGKGHDGLYQGLSTATKDTYDALHMQALPPR Amino acid sequence of CAR2: SEQ ID NO: 12
MALPVTALLLPLALLLHAARPDVQITQSPSYLAASPGETITINCRASKSISKDLAWYQEKPGKTNKL
LIYSGSTLQSGIPSRFSGSGSGTDFTLTISSLEPEDFAMYYCQQHNKYPYTFGGGTKLEIKGGGGSG
GGGSGGGGSQVQLQQPGAELVRPGASVKLSCKASGYTFTSYWMNWVKQRPDQGLEWIGRIDPY
DSETHYNQKFKDKAILTVDKSSSTAYMQLSSLTSEDSAVYYCARGNWDDYWGQGTTLTVSSTST
TTPAPRPPTPAPTIASQPLSLRPEACRPAAGGAVHTRGLDFACDIYIWAPLAGTCGVLLLSLVITLYC
KRGRKKLLYIFKQPFMRPVQTTQEEDGCSCRFPEEEEGGCELRVKFSRSADAPAYQQGQNQLYNE
LNLGRREEYDVLDKRRGRDPEMGGKPRRKNIPQEGLYNELQKDKMAEAYSEIGMKGERRRGKGH
DGLYQGLSTATKDTYDALHMQALPPR Amino acid sequence of CAR3: SEQ ID NO: 13
MALPVTALLLPLALLLHAARPMADYKDIVMTQSHKFMSTSVGDRVNITCKASQNVDSAVAWYQ
QKPGQSPKALIYSASYRYSGVPDRFTGRGSGTDFTLTISSVQAEDLAVYYCQQYSTPWTFGGGTK
LEIKRGGGGSGGGGSGGGGSEVKLVESGGGLVQPGGSLSLSCAASGFTFTDYYMSWVRQPPGKA
LEWLALIRSKADGYTTEYSASVKGRFTLSRDDSQSILYLQMNALRPEDSATYYCARDAAYYSYYS
PEGAMDYWGQGTSVTVSSTSTTTPAPRPPTPAPTIASQPLSLRPEACRPAAGGAVHTRGLDFACDI
YIWAPLAGTCGVLLLSLVITLYCKRGRICKLLYIFKQPFMRPVQTTQEEDGCSCRFPEEEEGGCELR
VKFSRSADAPAYQQGQNQLYNELNLGRREEYDVLDKRRGRDPEMGGKPRRKNIPQEGLYNELQK
DKMAEAYSEIGMKGERRRGKGHDGLYQGLSTATKDTYDALHMQALPPR Amino acid sequence of CRL1: SEQ ID NO: 14
MSRLPVLLLLQLLVRPGLQAPMTQTTPLKTSWVNCSNMIDEIITHLKQPPLPLLDFNNLNGEDQDIL
MENNLRRPNLEAFNRAVKSLQNASAIESILKNILLPCLPLATAAPTRHPIHIKDGDWNEFRRKLTFYL
KTLENAQAQQTTLSLAIFTSTTTPAPRPPTPAPTIASQPLSLRPEACRPAAGGAVHTRGLDFACDIYI
WAPLAGTCGVLLLSLVITLYCKRGRKKLLYIFKQPFMRPVQTTQLEDGCSCRFPEELEGGCELRVK
FSRSADAPAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR Amino acid sequence of CRL2: SEQ ID NO: 15
MSRLPVLLLLQLLVRPGLQAPMTQTTPLKTSWVNCSNMIDEIITHLKQPPLPLLDFNNLNGEDQDIL
MENNLRRPNLEAFNRAVKSLQNASAIESILKNILLPCLPLATAAPTRHPIHIKDGDWNEFRRKLTFYL
KTLENAQAQQTTLSLAIFTSTTTPAPRPPTPAPTIASQPLSLRPEACRPAAGGAVHTRGLDFACDRS
KRSRLLHSDYMNMTPRRPGPTRKHYQPYAPPRDFAAYRSRVKFSRSADAPAYQQGQNQLYNELN
LGRREEYDVLDKRRGRDPEMGGKPRRKNIPQEGLYNELQKDKMALAYSEIGMKGERRRGKGHDG
LYQGLSTATKDTYDALHMQALPPR Amino acid sequence of CRL3: SEQ ID NO: 16
MSRLPVLLLLQLLVRPGLQAPMTQTTPLKTSWVNCSNMIDEIITHLKQPPLPLLDFNNLNGEDQDIL
MENNLRRPNLEAFNRAVKSLQNASAIESILKNILLPCLPLATAAPTRHPIHIKDGDWNEFRRKLTFYL
KTLENAQAQQTTLSLAIFTSTTTPAPRPPTPAPTIASQPLSLRPEACRPAAGGAVHTRGLDFACDRS
KRSRLLHSDYMNMTPRRPGPTRKHYQPYAPPRDFAAYRSIYIWAPLAGTCGVLLLSLVITLYCKRG
RICKLLYIFKQPFMRPVQTTQLEDGCSCRFPEELEGGCELRVKFSRSADAPAYQQGQNQLYNELNL
GRREEYDVLDKRRGRDPEMGGKPRRKNPQEGLYNELQKDKMALAYSEIGMKGERRRGKGHDGL
YQGLSTATKDTYDALHMQALPPR Amino acid sequence of CRL4: SEQ ID NO: 17
MALPVTALLLPLALLLHAARPAPMTQTTPLKTSWVNCSNMIDEIITHLKQPPLPLLDFNNLNGEDQ
DILMENNLRRPNLEAFNRAVKSLQNASAIESILKNILLPCLPLATAAPTRHPIHIKDGDWNEFRRKLT
FYLKTLENAQAQQTTLSLAIFTSTTTPAPRPPTPAPTIASQPLSLRPEACRPAAGGAVHTRGLDFAC
DIYIWAPLAGTCGVLLLSLVITLYCKRGRKKLLYIFKQPFMRPVQTTQLEDGCSCRFPEELEGGCEL
RVKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR Amino acid sequence of CRL5: SEQ ID NO: 18
MALPVTALLLPLALLLHAARPAPMTQTTPLKTSWVNCSNMIDEIITHLKQPPLPLLDFNNLNGEDQ
DILMENNLRRPNLEAFNRAVKSLQNASAIESILKNILLPCLPLATAAPTRHPIHIKDGDWNEFRRKLT
FYLKTLENAQAQQTTLSLAIFTSTTTPAPRPPTPAPTIASQPLSLRPEACRPAAGGAVHTRGLDFAC
DRSKRSRLLHSDYMNMTPRRPGPTRKHYQPYAPPRDFAAYRSRVKFSRSADAPAYQQGQNQLYN
ELNLGRREEYDVLDKRRGRDPEMGGKPRRKNPQEGLYNELQKDKIVIALAYSEIGMKGERRRGKG
HDGLYQGLSTATKDTYDALHMQALPPR Amino acid sequence of CRL6: SEQ ID NO: 19
MALPVTALLLPLALLLHAARPAPMTQTTPLKTSWVNCSNMIDEIITHLKQPPLPLLDFNNLNGEDQ
DILMENNLRRPNLEAFNRAVKSLQNASAIESILKNILLPCLPLATAAPTRHPIHIKDGDWNEFRRKLT
FYLKTLENAQAQQTTLSLAIFTSTTTPAPRPPTPAPTIASQPLSLRPEACRPAAGGAVHTRGLDFAC
DRSKRSRLLHSDYMNMTPRRPGPTRKHYQPYAPPRDFAAYRSIYIWAPLAGTCGVLLLSLVITLYC
KRGRKKLLYIFKQPFMRPVQTTQLEDGCSCRFPEELEGGCELRVKFSRSADAPAYQQGQNQLYNE
```

```
                            SEQUENCE LISTING

LNLGRREEYDVLDKRRGRDPEMGGKPRRKNIPQEGLYNELQKDKMALAYSEIGMKGERRRGKGH
DGLYQGLSTATKDTYDALHMQALPPR

Nucleotide sequence of IL-3 receptor binding domain: SEQ ID NO: 20  1-399
GCCCCAATGACACAGACAACCCCACTGAAAACCTCTTGGGTGAACTGCAGCAATATGATCGA
CGAGATCATCACACACCTGAAGCAGCCCCTCTGCCCCTGCTGGATTTCAACAATCTGAACGG
CGAGGACCAGGATATCCTGATGGAGAACAATCTGAGACGGCCCAACCTGGAGGCCTTTAATC
GGGCCGTGAAGAGCCTGCAGAACGCCAGCGCCATCGAGTCCATCCTGAAGAATCTGCTGCCA
TGTCTGCCACTGGCAACCGCAGCACCTACAAGGCACCCAATCCACATCAAGGACGGCGATTG
GAATGAGTTCAGGCGCAAGCTGACCTTTTACCTGAAAACACTGGAAAACGCTCAGGCACAGC
AGACCACACTGTCACTGGCAATCTTC Nucleotide sequence of IL-3 receptor binding domain: SEQ ID NO: 21  1-372
GCCCCAATGACACAGACAACCCCACTGAAAACCTCTTGGGTGAACTGCAGCAATATGATCGA
CGAGATCATCACACACCTGAAGCAGCCCCTCTGCCCCTGCTGGATTTCAACAATCTGAACGG
CGAGGACCAGGATATCCTGATGGAGAACAATCTGAGACGGCCCAACCTGGAGGCCTTTAATC
GGGCCGTGAAGAGCCTGCAGAACGCCAGCGCCATCGAGTCCATCCTGAAGAATCTGCTGCCA
TGTCTGCCACTGGCAACCGCAGCACCTACAAGGCACCCAATCCACATCAAGGACGGCGATTG
GAATGAGTTCAGGCGCAAGCTGACCTTTTACCTGAAAACACTGGAAAACGCTCAGGCACAG Nucleotide sequence of IL-3 signal peptide: SEQ ID NO: 22
ATGAGTAGACTGCCCGTGCTGCTGCTGCTGCAGCTGCTGGTGCGACCTGGACTGCAG Nucleotide sequence of CD8α signal peptide: SEQ ID NO: 23
ATGGCCTTACCAGTGACCGCCTTGCTCCTGCCGCTGGCCTTGCTGCTCCACGCCGCCAGGCCG Nucleotide sequence of CD8α hinge region: SEQ ID NO: 24
ACCACGACGCCAGCGCCGCGACCACCAACACCGGCGCCCACCATCGCGTCGCAGCCCCTGTC
CCTGCGCCCAGAGGCGTGCCGGCCAGCGGCGGGGGCGCAGTGCACACGAGGGGGCTGGACT
TCGCCTGTGAT Nucleotide sequence of CD8α transmembrane region: SEQ ID NO: 25
ATCTACATCTGGGCGCCCTTGGCCGGGACTTGTGGGGTCCTTCTCCTGTCACTGGTTATCACCC
TTTACTGC Nucleotide sequence of CD28 transmembrane region: SEQ ID NO: 26
TTCCCGGACCTTCTAAGCCCTTTTGGGTGCTGGTGGTGGTTGGTGGAGTCCTGGCTTGCTATAG
CTTGCTAGTAACAGTGG Nucleotide sequence of CD3z transmembrane region: SEQ ID NO: 27
AGAGTGAAGTTCAGCAGGAGCGCAGACGCCCCCGCGTACCAGCAGGGCCAGAACCAGCTCTA
TAACGAGCTCAATCTAGGACGAAGAGAGGAGTACGATGTTTTGGACAAGAGACGTGGCCGGG
ACCCTGAGATGGGGGGAAAGCCGAGAAGGAAGAACCCTCAGGAAGGCCTGTACAATGAACT
GCAGAAAGATAAGATGGCGGAGGCCTACAGTGAGATTGGGATGAAAGGCGAGCGCCGGAGG
GGCAAGGGGCACGATGGCCTTTACCAGGGTCTCAGTACAGCCACCAAGGACACCTACGACGC
CCTTCACATGCAGGCCCTGCCCCCTCGC Nucleotide sequence of 4-1BB intracellular region: SEQ ID NO: 28
AAACGGGGCAGAAAGAAACTCCTGTATATATTCAAACAACCATTTATGAGACCAGTACAAAC
TACTCAAGAGGAAGATGGCTGTAGCTGCCGATTTCCAGAAGAAGAAGAAGGAGGATGTGAAC
TG Nucleotide sequence of CD28 intracellular region: SEQ ID NO: 29
CCTTTATTATTTTCTGGGTGAGGAGTAAGAGGAGCAGGCTCCTGCACAGTGACTACATGAACA
TGACTCCCCGCCGCCCCGGGCCCACCCGCAAGCATTACCAGCCCTATGCCCCACCACGCGACT
TCGCAGCCTATCGCTCC Nucleotide sequence of CAR1: SEQ ID NO: 30
ATGGCTCTGCCCGTGACCGCACTGCTGCTGCCCCTGGCTCTGCTGCTGCACGCCGCCCGACCT
GGAAGCGACATCGTCCTGACACAGAGCCCAGCATCCCTGGCCGTGTCCCTGGGACAGCGGGC
CACCATCTCTTGCAGAGCCTCTGAGAGCGTGGACAACTACGGCAATACATTCATGCACTGGTA
TCAGCAGAAGCCCGGCCAGCCCCCTAAGCTGCTGATCTACCGGGCCTCCAACCTGGAGTCTGG
CATCCCCGCAAGGTTCTCCGGATCTGGCAGCCGCACCGACTTTACCCTGACAATCAACCCTGT
GGAGGCCGACGATGTGGCCACATACTATTGCCAGCAGAGCAATGAGGATCCACCCACCTTTG
GCGCCGGCACAAAGCTGGAGCTGAAGGGAGGAGGAGGATCCGGAGGAGGAGGAAGCTCCGG
AGGAGGCTCTCAGATCACGCTGGTGCAGAGCGGCCCTGAGCTGAAGAAGCCAGGCGAGACAG
TGAAGATCAGCTGTAAGGCCTCCGGCTACATCTTCACAAACTATGGCATGAATTGGGTGAAGC
AGGCCCCTGGCAAGTCTTTTAAGTGGATGGGCTGGATCAATACCTACACAGGCGAGTCTACCT
ATAGCGCCGATTTCAAGGGCCGGTTCGCCTTTAGCCTGGAGACAAGCGCCTCTACAGCCTACC
TGCACATCAACGACCTGAAGAATGAGGATACCGCCACATATTTTTGTGCCAGGTCAGGGGGGT
ATGATCCTATGGACTATTGGGGGCAGGGGACCTCCGTGACCGTCTCAAGCACTAGTACCACGA
CGCCAGCGCCGCGACCACCAACACCGGCGCCCACCATCGCGTCGCAGCCCCTGTCCCTGCGCC
CAGAGGCGTGCCGGCCAGCGGCGGGGGCGCAGTGCACACGAGGGGGCTGGACTTCGCCTGT
GATATCTACATCTGGGCGCCCTTGGCCGGGACTTGTGGGGTCCTTCTCCTGTCACTGGTTATCA
CCCTTTACTGCAAACGGGGCAGAAAGAAACTCCTGTATATATTCAAACAACCATTTATGAGAC
CAGTACAAACTACTCAAGAGGAAGATGGCTGTAGCTGCCGATTTCCAGAAGAAGAAGAAGGA
GGATGTGAACTGAGAGTGAAGTTCAGCAGGAGCGCAGACGCCCCCGCGTACCAGCAGGGCCA
```

```
GAACCAGCTCTATAACGAGCTCAATCTAGGACGAAGAGAGGAGTACGATGTTTTGGACAAGA
GACGTGGCCGGGACCCTGAGATGGGGGGAAAGCCGAGAAGGAAGAACCCTCAGGAAGGCCT
GTACAATGAACTGCAGAAAGATAAGATGGCGGAGGCCTACAGTGAGATTGGGATGAAAGGC
GAGCGCCGGAGGGGCAAGGGGCACGATGGCCTTTACCAGGGTCTCAGTACAGCCACCAAGGA
CACCTACGACGCCCTTCACATGCAGGCCCTGCCCCCTCGCTAA

Nucleotide sequence of CAR2: SEQ ID NO: 31
ATGGCCCTGCCCGTCACTGCCCTGCTGCTGCCCCTGGCCCTGCTGCTGCACGCCGCAAGACCC
GATGTCCAGATTACTCAGAGCCCATCCTACCTGGCCGCCTCTCCCGGCGAGACAATCACAATC
AACTGCAGGGCCTCCAAGTCTATCAGCAAGGACCTGGCCTGGTACCAGGAGAAGCCCGGCAA
GACCAATAAGCTGCTGATCTATTCCGGCTCTACACTGCAGTCTGGCATCCCTAGCAGGTTCAG
CGGATCCGGATCTGGAACCGACTTTACCCTGACAATCAGCTCCCTGGAGCCTGAGGATTTCGC
CATGTACTATTGCCAGCAGCACAACAAGTACCCATATACCTTTGGCGGCGGCACAAAGCTGGA
GATCAAGGGAGGAGGAGGAAGCGGAGGAGGAGGATCCGGCGGCGGCGGCTCTCAGGTGCAG
CTGCAGCAGCCCGGCGCCGAGCTGGTGCGGCCTGGAGCATCCGTGAAGCTGTCTTGTAAGGCC
AGCGGCTACACCTTCACATCCTATTGGATGAACTGGGTGAAGCAGCGGCCAGACCAGGGCCT
GGAGTGGATCGGCAGAATCGACCCCTACGATAGCGAGACACACTATAATCAGAAGTTTAAGG
ACAAGGCCATCCTGACCGTGGATAAGTCTAGCTCCACAGCCTATATGCAGCTGTCTAGCCTGA
CAAGCGAGGATTCCGCCGTGTACTATTGTGCTCGGGGAAACTGGGATGACTATTGGGGACAG
GGGACAACTCTGACCGTCTCAAGCACTAGTACCACGACGCCAGCGCCGCGACCACCAACACC
GGCGCCCACCATCGCGTCGCAGCCCCTGTCCCTGCGCCCAGAGGCGTGCCGGCCAGCGGCGG
GGGGCGCAGTGCACACGAGGGGCTGGACTTCGCCTGTGATATCTACATCTGGGCGCCCTTGG
CCGGGACTTGTGGGGTCCTTCTCCTGTCACTGGTTATCACCCTTTACTGCAAACGGGGCAGAA
AGAAACTCCTGTATATATTCAAACAACCATTTATGAGACCAGTACAAACTACTCAAGAGGAA
GATGGCTGTAGCTGCCGATTTCCAGAAGAAGAAGAAGGAGGATGTGAACTGAGAGTGAAGTT
CAGCAGGAGCGCAGACGCCCCCGCGTACCAGCAGGGCCAGAACCAGCTCTATAACGAGCTCA
ATCTAGGACGAAGAGAGGAGTACGATGTTTTGGACAAGAGACGTGGCCGGGACCCTGAGATG
GGGGGAAAGCCGAGAAGGAAGAACCCTCAGGAAGGCCTGTACAATGAACTGCAGAAAGATA
AGATGGCGGAGGCCTACAGTGAGATTGGGATGAAAGGCGAGCGCCGGAGGGGCAAGGGGCA
CGATGGCCTTTACCAGGGTCTCAGTACAGCCACCAAGGACACCTACGACGCCCTTCACATGCA
GGCCCTGCCCCCTCGCTAA Nucleotide sequence of CAR3: SEQ ID NO: 32
ATGGCTCTGCCTGTGACCGCACTGCTGCTGCCCCTGGCTCTGCTGCTGCACGCTGCCCGCCCTA
TGGCCGACTATAAAGACATTGTGATGACCCAGTCTCACAAGTTCATGTCTACAAGCGTGGGCG
ACCGGGTGAACATCACCTGCAAGGCCTCCCAGAATGTGGATTCTGCCGTGGCCTGGTACCAGC
AGAAGCCAGGCCAGTCCCCCAAGGCCCTGATCTATTCCGCCTCTTACCGGTATTCTGGAGTGC
CTGACAGGTTCACCGGAAGAGGAAGCGGCACAGATTTTACCCTGACAATCAGCTCCGTGCAG
GCAGAGGACCTGGCAGTGTACTATTGCCAGCAGTACTATAGCACCCCATGGACATTTGGCGGC
GGCACCAAGCTGGAGATCAAGGGGGGAGGAGGAAGCGGAGGAGGAGGATCCGGCGGCG
GCGGCTCTGAGGTGAAGCTGGTGGAGTCCGGAGGAGGCCTGGTGCAGCCAGGAGGCAGCCTG
TCCCTGTCTTGTGCCGCCAGCGGCTTCACCTTTACAGACTACTATATGTCCTGGGTCAGGCAGC
CACCTGGAAAGGCACTGGAGTGGCTGGCACTGATCAGGAGCAAGGCCGATGGCTACACCACA
GAGTATAGCGCCTCCGTGAAGGGCAGGTTCACCCTGTCCCGACGATTCTCAGAGCATCCTG
TACCTGCAGATGAACGCACTGCGCCTGAGGACTCCGCAACATACTATTGTGCCAGAGATGCC
GCCTACTATTCTTACTATTCACCAGAAGGGGCTATGGATTATTGGGGCAGGGGACAAGCGTC
ACCGTCTCATCATCAACTAGTACCACGACGCCAGCGCCGCGACCACCAACACCGGCGCCCACC
ATCGCGTCGCAGCCCCTGTCCCTGCGCCCAGAGGCGTGCCGGCCAGCGGCGGGGGGCGCAGT
GCACACGAGGGGCTGGACTTCGCCTGTGATATCTACATCTGGGCGCCCTTGGCCGGGACTTG
TGGGGTCCTTCTCCTGTCACTGGTTATCACCCTTTACTGCAAACGGGGCAGAAAGAAACTCCT
GTATATATTCAAACAACCATTTATGAGACCAGTACAAACTACTCAAGAGGAAGATGGCTGTA
GCTGCCGATTTCCAGAAGAAGAAGAAGGAGGATGTGAACTGAGAGTGAAGTTCAGCAGGAGC
GCAGACGCCCCCGCGTACCAGCAGGGCCAGAACCAGCTCTATAACGAGCTCAATCTAGGACG
AAGAGAGGAGTACGATGTTTTGGACAAGAGACGTGGCCGGGACCCTGAGATGGGGGGAAAG
CCGAGAAGGAAGAACCCTCAGGAAGGCCTGTACAATGAACTGCAGAAAGATAAGATGGCGG
AGGCCTACAGTGAGATTGGGATGAAAGGCGAGCGCCGGAGGGGCAAGGGGCACGATGGCCT
TTACCAGGGTCTCAGTACAGCCACCAAGGACACCTACGACGCCCTTCACATGCAGGCCCTGCC
CCCTCGCTAA Nucleotide sequence of CRL1: SEQ ID NO: 33
ATGAGTAGACTGCCCGTGCTGCTGCTGCTGCAGCTGCTGCTGCGACCTGGACTGCAGGCCCCA
ATGACACAGACAACCCCACTGAAAACCTCTTGGGTGAACTGCAGCAATATGATCGACGAGAT
CATCACACACCTGAAGCAGCCCCTCTGCCCCTGCTGGATTTCAACAATCTGAACGGCGAGGA
CCAGGATATCCTGATGGAGAACAATCTGAGACGGCCCAACCTGGAGGCCTTTAATCGGGCCG
TGAAGAGCCTGCAGAACGCCAGCGCCATCGAGTCCATCCTGAAGAATCTGCTGCCATGTCTGC
CACTGGCAACCGCAGCACCTACAAGGCACCCAATCCACATCAAGGACGGCGATTGGAATGAA
TTCAGGCGCAAGCTGACCTTTTACCTGAAAACACTGGAAAACGCTCAGGCACAGCAGACCAC
ACTGTCACTGGCAATCTTCACTAGTACCACGACGCCAGCGCCGCGACCACCAACACCGGCGCC
CACCATCGCGTCGCAGCCCCTGTCCCTGCGCCCAGAGGCGTGCCGGCCAGCGGCGGGGGGCG
CAGTGCACACGAGGGGCTGGACTTCGCCTGTGATATCTACATCTGGGCGCCCTTGGCCGGGA
CTTGTGGGGTCCTTCTCCTGTCACTGGTTATCACCCTTTACTGCAAACGGGGCAGAAAGAAAC
TCCTGTATATATTCAAACAACCATTTATGAGACCAGTACAAACTACTCAAGAGGAAGATGGCT
GTAGCTGCCGATTTCCAGAAGAAGAAGAAGGAGGATGTGAACTGAGAGTGAAGTTCAGCAGG
AGCGCAGACGCCCCCGCGTACCAGCAGGGCCAGAACCAGCTCTATAACGAGCTCAATCTAGG
ACGAAGAGAGGAGTACGATGTTTTGGACAAGAGACGTGGCCGGGACCCTGAGATGGGGGGA
AAGCCGAGAAGGAAGAACCCTCAGGAAGGCCTGTACAATGAACTGCAGAAAGATAAGATGG
CGGAGGCCTACAGTGAGATTGGGATGAAAGGCGAGCGCCGGAGGGGCAAGGGGCACGATGG
```

```
CCTTTACCAGGGTCTCAGTACAGCCACCAAGGACACCTACGACGCCCTTCACATGCAGGCCCT
GCCCCCTCGCTAA

Nucleotide sequence of CRL2: SEQ ID NO: 34
ATGAGTAGACTGCCCGTGCTGCTGCTGCTGCAGCTGCTGGTGCGACCTGGACTGCAGGCCCCA
ATGACACAGACAACCCCACTGAAAACCTCTTGGGTGAACTGCAGCAATATGATCGACGAGAT
CATCACACACCTGAAGCAGCCCCCTCTGCCCCTGCTGGATTTCAACAATCTGAACGGCGAGGA
CCAGGATATCCTGATGGAGAACAATCTGAGACGGCCCAACCTGGAGGCCTTTAATCGGGCCG
TGAAGAGCCTGCAGAACGCCAGCGCCATCGAGTCCATCCTGAAGAATCTGCTGCCATGTCTGC
CACTGGCAACCGCAGCACCTACAAGGCACCCAATCCACATCAAGGACGGCGATTGGAATGAG
TTCAGGCGCAAGCTGACCTTTTACCTGAAAACACTGGAAAACGCTCAGGCACAGCAGACCAC
ACTGTCACTGGCAATCTTCACTAGTACCACGACGCCAGCGCCGCGACCACCAACACCGGCGCC
CACCATCGCGTCGCAGCCCTGTCCCTGCGCCCAGAGGCGTGCCGGCCAGCGGCGGGGGCG
CAGTGCACACGAGGGGGCTGGACTTCGCCTGTGATATCTACATCTGGGCGCCCTTGGCCGGA
CTTGTGGGGTCCTTCTCCTGTCACTGGTTATCACCCTTTACTGCCCTTTATTATTTTCTGGGTGA
GGAGTAAGAGGAGCAGGCTCCTGCACAGTGACTACATGAACATGACTCCCCGCCGCCCGGG
CCCACCCGCAAGCATTACCAGCCCTATGCCCCACCACGCGACTTCGCAGCCTATCGCTCCAGA
GTGAAGTTCAGCAGGAGCGCAGACGCCCCCGCGTACCAGCAGGGCCAGAACCAGCTCTATAA
CGAGCTCAATCTAGGACGAAGAGAGGAGTACGATGTTTTGGACAAGAGACGTGGCCGGGACC
CTGAGATGGGGGGAAAGCCGAGAAGGAAGAACCCTCAGGAAGGCCTGTACAATGAACTGCA
GAAAGATAAGATGGCGGAGGCCTACAGTGAGATTGGGATGAAAGGCGAGCGCCGGAGGGGC
AAGGGGCACGATGGCCTTTACCAGGGTCTCAGTACAGCCACCAAGGACACCTACGACGCCCT
TCACATGCAGGCCCTGCCCCCTCGCTAA Nucleotide sequence of CRL3: SEQ ID NO: 35
ATGAGTAGACTGCCCGTGCTGCTGCTGCTGCAGCTGCTGGTGCGACCTGGACTGCAGGCCCCA
ATGACACAGACAACCCCACTGAAAACCTCTTGGGTGAACTGCAGCAATATGATCGACGAGAT
CATCACACACCTGAAGCAGCCCCCTCTGCCCCTGCTGGATTTCAACAATCTGAACGGCGAGGA
CCAGGATATCCTGATGGAGAACAATCTGAGACGGCCCAACCTGGAGGCCTTTAATCGGGCCG
TGAAGAGCCTGCAGAACGCCAGCGCCATCGAGTCCATCCTGAAGAATCTGCTGCCATGTCTGC
CACTGGCAACCGCAGCACCTACAAGGCACCCAATCCACATCAAGGACGGCGATTGGAATGAG
TTCAGGCGCAAGCTGACCTTTTACCTGAAAACACTGGAAAACGCTCAGGCACAGCAGACCAC
ACTGTCACTGGCAATCTTCACTAGTACCACGACGCCAGCGCCGCGACCACCAACACCGGCGCC
CACCATCGCGTCGCAGCCCTGTCCCTGCGCCCAGAGGCGTGCCGGCCAGCGGCGGGGGCG
CAGTGCACACGAGGGGGCTGGACTTCGCCTGTGATATCTACATCTGGGCGCCCTTGGCCGGA
CTTGTGGGGTCCTTCTCCTGTCACTGGTTATCACCCTTTACTGCCCTTTATTATTTTCTGGGTGA
GGAGTAAGAGGAGCAGGCTCCTGCACAGTGACTACATGAACATGACTCCCCGCCGCCCGGG
CCCACCCGCAAGCATTACCAGCCCTATGCCCCACCACGCGACTTCGCAGCCTATCGCTCCAAA
CGGGGCAGAAAGAAACTCCTGTATATATTCAAACAACCATTTATGAGACCAGTACAAACTACT
CAAGAGGAAGATGGCTGTAGCTGCCGATTTCCAGAAGAAGAAGAAGGAGGATGTGAACTGA
GAGTGAAGTTCAGCAGGAGCGCAGACGCCCCCGCGTACCAGCAGGGCCAGAACCAGCTCTAT
AACGAGCTCAATCTAGGACGAAGAGAGGAGTACGATGTTTTGGACAAGAGACGTGGCCGGGA
CCCTGAGATGGGGGGAAAGCCGAGAAGGAAGAACCCTCAGGAAGGCCTGTACAATGAACTG
CAGAAAGATAAGATGGCGGAGGCCTACAGTGAGATTGGGATGAAAGGCGAGCGCCGGAGGG
GCAAGGGGCACGATGGCCTTTACCAGGGTCTCAGTACAGCCACCAAGGACACCTACGACGCC
CTTCACATGCAGGCCCTGCCCCCTCGCTAA Nucleotide sequence of CRL4: SEQ ID NO: 36
ATGGCCTTACCAGTGACCGCCTTGCTCCTGCCGCTGGCCTTGCTGCTCCACGCCGCCAGGCCG
GCCCCAATGACACAGACAACCCCACTGAAAACCTCTTGGGTGAACTGCAGCAATATGATCGA
CGAGATCATCACACACCTGAAGCAGCCCCCTCTGCCCCTGCTGGATTTCAACAATCTGAACGG
CGAGGACCAGGATATCCTGATGGAGAACAATCTGAGACGGCCCAACCTGGAGGCCTTTAATC
GGGCCGTGAAGAGCCTGCAGAACGCCAGCGCCATCGAGTCCATCCTGAAGAATCTGCTGCCA
TGTCTGCCACTGGCAACCGCAGCACCTACAAGGCACCCAATCCACATCAAGGACGGCGATTG
GAATGAGTTCAGGCGCAAGCTGACCTTTTACCTGAAAACACTGGAAAACGCTCAGGCACAGC
AGACCACACTGTCACTGGCAATCTTCACTAGTACCACGACGCCAGCGCCGCGACCACCAACAC
CGGCGCCCACCATCGCGTCGCAGCCCTGTCCCTGCGCCCAGAGGCGTGCCGGCCAGCGCG
GGGGCGCAGTGCACACGAGGGGGCTGGACTTCGCCTGTGATATCTACATCTGGGCGCCCTTG
GCCGGGACTTGTGGGGTCCTTCTCCTGTCACTGGTTATCACCCTTTACTGCAAACGGGGCAGA
AAGAAACTCCTGTATATATTCAAACAACCATTTATGAGACCAGTACAAACTACTCAAGAGGA
AGATGGCTGTAGCTGCCGATTTCCAGAAGAAGAAGAAGGAGGATGTGAACTGAGAGTGAAGT
TCAGCAGGAGCGCAGACGCCCCCGCGTACCAGCAGGGCCAGAACCAGCTCTATAACGAGCTC
AATCTAGGACGAAGAGAGGAGTACGATGTTTTGGACAAGAGACGTGGCCGGGACCCTGAGAT
GGGGGGAAAGCCGAGAAGGAAGAACCCTCAGGAAGGCCTGTACAATGAACTGCAGAAAGAT
AAGATGGCGGAGGCCTACAGTGAGATTGGGATGAAAGGCGAGCGCCGGAGGGGCAAGGGGC
ACGATGGCCTTTACCAGGGTCTCAGTACAGCCACCAAGGACACCTACGACGCCCTTCACATGC
AGGCCCTGCCCCCTCGCTAA Nucleotide sequence of CRL5: SEQ ID NO: 37
ATGGCCTTACCAGTGACCGCCTTGCTCCTGCCGCTGGCCTTGCTGCTCCACGCCGCCAGGCCG
GCCCCAATGACACAGACAACCCCACTGAAAACCTCTTGGGTGAACTGCAGCAATATGATCGA
CGAGATCATCACACACCTGAAGCAGCCCCCTCTGCCCCTGCTGGATTTCAACAATCTGAACGG
CGAGGACCAGGATATCCTGATGGAGAACAATCTGAGACGGCCCAACCTGGAGGCCTTTAATC
GGGCCGTGAAGAGCCTGCAGAACGCCAGCGCCATCGAGTCCATCCTGAAGAATCTGCTGCCA
TGTCTGCCACTGGCAACCGCAGCACCTACAAGGCACCCAATCCACATCAAGGACGGCGATTG
GAATGAGTTCAGGCGCAAGCTGACCTTTTACCTGAAAACACTGGAAAACGCTCAGGCACAGC
AGACCACACTGTCACTGGCAATCTTCACTAGTACCACGACGCCAGCGCCGCGACCACCAACAC
```

```
CGGCGCCCACCATCGCGTCGCAGCCCCTGTCCCTGCGCCCAGAGGCGTGCCGGCCAGCGGCG
GGGGGCGCAGTGCACACGAGGGGGCTGGACTTCGCCTGTGATATCTACATCTGGGCGCCCTTG
GCCGGGACTTGTGGGGTCCTTCTCCTGTCACTGGTTATCACCCTTTACTGCCCTTTATTATTTC
TGGGTGAGGAGTAAGAGGAGCAGGCTCCTGCACAGTGACTACATGAACATGACTCCCCGCCG
CCCCGGGCCCACCCGCAAGCATTACCAGCCCTATGCCCCACCACGCGACTTCGCAGCCTATCG
CTCCAGAGTGAAGTTCAGCAGGAGCGCAGACGCCCCCGCGTACCAGCAGGGCCAGAACCAGC
TCTATAACGAGCTCAATCTAGGACGAAGAGAGGAGTACGATGTTTTGGACAAGAGACGTGGC
CGGGACCCTGAGATGGGGGAAAGCCGAGAAGGAAGAACCCTCAGGAAGGCCTGTACAATG
AACTGCAGAAAGATAAGATGGCGGAGGCCTACAGTGAGATTGGGATGAAAGGCGAGCGCCG
GAGGGGCAAGGGGCACGATGGCCTTTACCAGGGTCTCAGTACAGCCACCAAGGACACCTACG
ACGCCCTTCACATGCAGGCCCTGCCCCCTCGC

Nucleotide sequence of CRL6: SEQ ID NO: 38
ATGGCCTTACCAGTGACCGCCTTGCTCCTGCCGCTGGCCTTGCTGCTCCACGCCGCCAGGCCG
GCCCCAATGACACAGACAACCCCACTGAAAACCTCTTGGGTGAACTGCAGCAATATGATCGA
CGAGATCATCACACACCTGAAGCAGCCCCCTCTGCCCCTGCTGGATTTCAACAATCTGAACGG
CGAGGACCAGGATATCCTGATGGAGAACAATCTGAGACGGCCCAACCTGGAGGCCTTTAATC
GGGCCGTGAAGAGCCTGCAGAACGCCAGCGCCATCGAGTCCATCCTGAAGAATCTGCTGCCA
TGTCTGCCACTGGCAACCGCAGCACCTACAAGGCACCCAATCCACATCAAGGACGGCGATTG
GAATGAGTTCAGGCGCAAGCTGACCTTTTACCTGAAAACACTGGAAAACGCTCAGGCACAGC
AGACCACACTGTCACTGGCAATCTTCACTAGTACCACGACGCAGCGCCGCGACCACCAACAC
CGGCGCCCACCATCGCGTCGCAGCCCCTGTCCCTGCGCCCAGAGGCGTGCCGGCCAGCGGCG
GGGGGCGCAGTGCACACGAGGGGGCTGGACTTCGCCTGTGATATCTACATCTGGGCGCCCTTG
GCCGGGACTTGTGGGGTCCTTCTCCTGTCACTGGTTATCACCCTTTACTGCCCTTTATTATTTC
TGGGTGAGGAGTAAGAGGAGCAGGCTCCTGCACAGTGACTACATGAACATGACTCCCCGCCG
CCCCGGGCCCACCCGCAAGCATTACCAGCCCTATGCCCCACCACGCGACTTCGCAGCCTATCG
CTCCAAACGGGGCAGAAAGAAACTCCTGTATATATTCAAACAACCATTTATGAGACCAGTAC
AAACTACTCAAGAGGAAGATGGCTGTAGCTGCCGATTTCCAGAAGAAGAAGAAGGAGGATGT
GAACTGAGAGTGAAGTTCAGCAGGAGCGCAGACGCCCCCGCGTACCAGCAGGGCCAGAACCA
GCTCTATAACGAGCTCAATCTAGGACGAAGAGAGGAGTACGATGTTTTGGACAAGAGACGTG
GCCGGGACCCTGAGATGGGGGAAAGCCGAGAAGGAAGAACCCTCAGGAAGGCCTGTACAA
TGAACTGCAGAAAGATAAGATGGCGGAGGCCTACAGTGAGATTGGGATGAAAGGCGAGCGC
CGGAGGGGCAAGGGGCACGATGGCCTTTACCAGGGTCTCAGTACAGCCACCAAGGACACCTA
CGACGCCCTTCACATGCAGGCCCTGCCCCCTCGCTAA IL-3 nucleotide sequence after the codon optimization: SEQ ID NO: 39
ATGAGTAGACTGCCCGTGCTGCTGCTGCTGCAGCTGCTGGTGCGACCTGGACTGCAGGCCCCA
ATGACACAGACAACCCCACTGAAAACCTCTTGGGTGAACTGCAGCAATATGATCGACGAGAT
CATCACACACCTGAAGCAGCCCCCTCTGCCCCTGCTGGATTTCAACAATCTGAACGGCGAGGA
CCAGGATATCCTGATGGAGAACAATCTGAGACGGCCCAACCTGGAGGCCTTTAATCGGGCCG
TGAAGAGCCTGCAGAACGCCAGCGCCATCGAGTCCATCCTGAAGAATCTGCTGCCATGTCTGC
CACTGGCAACCGCAGCACCTACAAGGCACCCAATCCACATCAAGGACGGCGATTGGAATGAG
TTCAGGCGCAAGCTGACCTTTTACCTGAAAACACTGGAAAACGCTCAGGCACAGCAGACCAC
ACTGTCACTGGCAATCTTC IL-3 amino acid sequence: SEQ ID NO: 40
MSRLPVLLLLQLLVRPGLQAPMTQTTPLKTSWVNCSNMIDEIITHLKQPPLPLLDFNNLNGEDQDIL
MENNLRRPNLEAFNRAVKSLQNASAIESILKNLLPCLPLATAAPTRHPIHIKDGDWNEFRRKLTFYL
KTLENAQAQQTTLSLAIF
```

The invention claimed is:

1. A human CD123-targeting chimeric receptor ligand, comprising an IL-3 molecule-based CD123 binding domain, a transmembrane region, and an intracellular signaling domain.

2. The human CD123-targeting chimeric receptor ligand according to claim 1, wherein the CD123 binding domain comprises at least 100 contiguous amino acid residues of SEQ ID NO: 1.

3. The human CD123-targeting chimeric receptor ligand according to claim 1, wherein the CD123 binding domain comprises an amino acid sequence having 95% to 99% identity to SEQ ID NO: 1 or SEQ ID NO: 2.

4. The human CD123-targeting chimeric receptor ligand according to claim 1, wherein the chimeric receptor ligand comprises two or more IL-3 molecule-based CD123 binding domains.

5. The human CD123-targeting chimeric receptor ligand according to claim 1, wherein the transmembrane region is selected from CD4, CD8α, CD28, PD1, and 4-1BB transmembrane regions.

6. The human CD123-targeting chimeric receptor ligand according to claim 1, wherein the intracellular signaling domain comprises a CD3 signaling domain, and optionally may further comprise a co-stimulatory signaling domain selected from the group consisting of CD27, CD28, 4-1BB, OX40, CD30, CD40, lymphocyte function-associated antigen-1 (LFA-1), CD2, CD7, LIGHT, NKG2C, B7-H3, and CD83-specific binding ligands or any combination thereof.

7. The human CD123-targeting chimeric receptor ligand according to claim 6, further comprising the co-stimulatory signaling domain selected from the CD28 and 4-1BB signaling domains.

8. The human CD123-targeting chimeric receptor ligand according to claim 1, further comprising an extracellular signal peptide.

9. The human CD123-targeting chimeric receptor ligand according to claim 8, wherein the extracellular signal peptide comprises a CD8α, GM-CSFRα, CD4, or IL-3 signal peptide.

10. A nucleic acid molecule encoding the human CD123-targeting chimeric receptor ligand according to claim 1.

11. A genetically engineered immune cell, comprising the nucleic acid molecule according to claim 10.

12. The genetically engineered immune cell according to claim 11, wherein the immune cell is selected from g T-lymphocyte cell, NK cell, and immune cell from culturing and differentiation of a hematopoietic stem cell, pluripotent stem cell and embryonic stem cell, respectively.

13. The genetically engineered immune cell according to claim 12, wherein the immune cell is a T-lymphocyte cell.

14. The human CD123-targeting chimeric receptor ligand according to claim 1, wherein:
the transmembrane region comprises a CD4, CD8α, CD28, PD1, or 4-1BB transmembrane region, and
the intracellular signaling domain comprises a CD3 signaling domain, and optionally may further comprise a co-stimulatory signaling domain selected from the group consisting of CD27, CD28, 4-1BB, OX40, CD30, CD40, lymphocyte function-associated antigen-1 (LFA-1), CD2, CD7, LIGHT, NKG2C, B7-H3, and CD83-specific binding ligands or any combination thereof.

15. The human CD123-targeting chimeric receptor ligand according to claim 1, wherein the CD123 binding domain comprises the amino acid sequence set forth in SEQ ID NO: 1 or SEQ ID NO: 2.

16. The human CD123-targeting chimeric receptor ligand according to claim 1, further comprising an extracellular signal peptide and a hinge region.

17. The human CD123-targeting chimeric receptor ligand according to claim 16, wherein:
the extracellular signal peptide comprises a CD8α, GM-CSFRα, CD4, or IL-3 signal peptide;

the hinge region is a CD8α hinge region;
the transmembrane region comprises a CD4, CD8α, CD28, PD1, or 4-1BB transmembrane region; and
the intracellular signaling domain comprises a CD3 signaling domain, and optionally may further comprise a co-stimulatory signaling domain selected from the group consisting of CD27, CD28, 4-1BB, OX40, CD30, CD40, lymphocyte function-associated antigen-1 (LFA-1), CD2, CD7, LIGHT, NKG2C, B7-H3, and CD83-specific binding ligands or any combination thereof.

18. The human CD123-targeting chimeric receptor ligand according to claim 17, comprising:
   a) the IL-3 signal peptide, the CD123 binding domain, the CD8α hinge region, the CD8α transmembrane region, the 4-1BB co-stimulatory signaling domain, and the CD3 signaling domain, and wherein the amino acid sequence of the human CD123-targeting chimeric receptor ligand comprises SEQ ID NO: 14 or an amino acid sequence having 95%-99% identity thereto;
   b) the IL-3 signal peptide, the CD123 binding domain, the CD8α hinge region, the CD28 co-stimulatory signaling domain, the CD8α transmembrane region, the 4-1BB co-stimulatory signaling domain, and the CD3 signaling domain, and wherein the amino acid sequence of the human CD123-targeting chimeric receptor ligand comprises SEQ ID NO: 16 or an amino acid sequence having 95%-99% identity thereto;
   c) the CD8α signal peptide, the CD123 binding domain, the CD8α hinge region, the CD8α transmembrane region, the 4-1BB co-stimulatory signaling domain, and the CD3 signaling domain, and wherein the amino acid sequence of the human CD123-targeting chimeric receptor ligand comprises SEQ ID NO: 17 or an amino acid sequence having 95%-99% identity thereto; or
   d) the CD8α signal peptide, the CD123 binding domain, the CD8α hinge region, the CD28 co-stimulatory signaling domain, the CD8α transmembrane region, the 4-1BB co-stimulatory signaling domain, and the CD3 signaling domain, and wherein the amino acid sequence of the human CD123-targeting chimeric receptor ligand comprises SEQ ID NO: 19 or an amino acid sequence having 95%-99% identity thereto.

19. A nucleic acid molecule encoding the human CD123-targeting chimeric receptor ligand according to claim 18, wherein:
   a) the nucleic acid molecule encodes SEQ ID NO: 14 and comprises the nucleotide sequence set forth as SEQ ID NO: 33;
   b) the nucleic acid molecule encodes SEQ ID NO: 16 and comprises the nucleotide sequence set forth as SEQ ID NO: 35;
   c) the nucleic acid molecule encodes SEQ ID NO: 17 and comprises the nucleotide sequence set forth as SEQ ID NO: 36; or
   d) the nucleic acid molecule encodes SEQ ID NO: 19 and comprises the nucleotide sequence set forth as SEQ ID NO: 38.

20. The human CD123-targeting chimeric receptor ligand according to claim 17, comprising:
   a) the IL-3 signal peptide, the CD123 binding domain, the CD8α hinge region, the CD8α transmembrane region, the CD28 co-stimulatory signaling domain, and the CD3 signaling domain, and wherein the IL-3 signal peptide, wherein the CD123 binding domain, the CD8α hinge region, the CD8α transmembrane region, the CD28 co-stimulatory signaling domain, and the CD3 signaling domain comprise the amino acid sequences set forth as SEQ ID NOs: 3, 1, 5, 6, 10, and 8, respectively; or
   b) the CD8α signal peptide, the CD123 binding domain, the CD8α hinge region, the CD8α transmembrane region, the CD28 co-stimulatory signaling domain, and the CD3 signaling domain, wherein the CD8α signal peptide, the CD123 binding domain, the CD8α hinge region, the CD8α transmembrane region, the CD28 co-stimulatory signaling domain, and the CD3 signaling domain comprise the amino acid sequences set forth as SEQ ID NOs: 4, 1, 5, 6, 10, and 8, respectively.

21. A nucleic acid molecule encoding a nucleotide sequence of the human CD123-targeting chimeric receptor ligand according to claim 20.

22. A method for treating a tumor in a subject, comprising administering to the subject an effective amount of the genetically engineered immune cell according to claim 11.

23. The method of claim 22, wherein the tumor is a malignant blood tumor.

* * * * *

SEQUENCE LISTING

<160> NUMBER OF SEQ ID NOS: 40

<210> SEQ ID NO 1
<211> LENGTH: 133
<212> TYPE: PRT
<213> ORGANISM: Artificial Sequence
<220> FEATURE:
<223> OTHER INFORMATION: Amino acid sequence of IL-3 receptor binding domain

<400> SEQUENCE: 1

Ala Pro Met Thr Gln Thr Thr Pro Leu Lys Thr Ser Trp Val Asn Cys
1               5                   10                  15

Ser Asn Met Ile Asp Glu Ile Ile Thr His Leu Lys Gln Pro Pro Leu
            20                  25                  30

Pro Leu Leu Asp Phe Asn Asn Leu Asn Gly Glu Asp Gln Asp Ile Leu
        35                  40                  45

Met Glu Asn Asn Leu Arg Arg Pro Asn Leu Glu Ala Phe Asn Arg Ala
        50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Arg Lys Leu Thr
                100                 105                 110

Phe Tyr Leu Lys Thr Leu Glu Asn Ala Gln Ala Gln Gln Thr Thr Leu
            115                 120                 125

Ser Leu Ala Ile Phe
        130

<210> SEQ ID NO 2
<211> LENGTH: 124
<212> TYPE: PRT
<213> ORGANISM: Artificial Sequence
<220> FEATURE:
<223> OTHER INFORMATION: Amino acid sequence of IL-3 receptor binding
      domain

<400> SEQUENCE: 2

Ala Pro Met Thr Gln Thr Thr Pro Leu Lys Thr Ser Trp Val Asn Cys
 1               5                  10                  15

Ser Asn Met Ile Asp Glu Ile Ile Thr His Leu Lys Gln Pro Pro Leu
             20                  25                  30

Pro Leu Leu Asp Phe Asn Asn Leu Asn Gly Glu Asp Gln Asp Ile Leu
         35                  40                  45

Met Glu Asn Asn Leu Arg Arg Pro Asn Leu Glu Ala Phe Asn Arg Ala
        50                  55                  60

Val Lys Ser Leu Gln Asn Ala Ser Ala Ile Glu Ser Ile Leu Lys Asn
 65                  70                  75                  80

Leu Leu Pro Cys Leu Pro Leu Ala Thr Ala Ala Pro Thr Arg His Pro
                 85                  90                  95

Ile His Ile Lys Asp Gly Asp Trp Asn Glu Phe Arg Arg Lys Leu Thr
                100                 105                 110

Phe Tyr Leu Lys Thr Leu Glu Asn Ala Gln Ala Gln
            115                 120

<210> SEQ ID NO 3
<211> LENGTH: 19
<212> TYPE: PRT
<213> ORGANISM: Artificial Sequence
<220> FEATURE:
<223> OTHER INFORMATION: Amino acid sequence of IL-3 signal peptide

<400> SEQUENCE: 3

Met Ser Arg Leu Pro Val Leu Leu Leu Gln Leu Leu Val Arg Pro
 1               5                  10                  15

Gly Leu Gln

<210> SEQ ID NO 4
<211> LENGTH: 21
<212> TYPE: PRT
<213> ORGANISM: Artificial Sequence
<220> FEATURE:
<223> OTHER INFORMATION: Amino acid sequence of CD8 signal peptide -continued

```
<400> SEQUENCE: 4

Met Ala Leu Pro Val Thr Ala Leu Leu Leu Pro Leu Ala Leu Leu Leu
1               5                   10                  15

His Ala Ala Arg Pro
            20

<210> SEQ ID NO 5
<211> LENGTH: 45
<212> TYPE: PRT
<213> ORGANISM: Artificial Sequence
<220> FEATURE:
<223> OTHER INFORMATION: Amino acid sequence of CD8 hinge region

<400> SEQUENCE: 5

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 6
<211> LENGTH: 24
<212> TYPE: PRT
<213> ORGANISM: Artificial Sequence
<220> FEATURE:
<223> OTHER INFORMATION: Amino acid sequence of CD8 transmembrane region

<400> SEQUENCE: 6

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 7
<211> LENGTH: 27
<212> TYPE: PRT
<213> ORGANISM: Artificial Sequence
<220> FEATURE:
<223> OTHER INFORMATION: Amino acid sequence of CD28 transmembrane
      region

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 8
<211> LENGTH: 112
<212> TYPE: PRT
<213> ORGANISM: Artificial Sequence
<220> FEATURE:
<223> OTHER INFORMATION: Amino acid sequence of CD3z

<400> SEQUENCE: 8

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 9
<211> LENGTH: 42
<212> TYPE: PRT
<213> ORGANISM: Artificial Sequence
<220> FEATURE:
<223> OTHER INFORMATION: Amino acid sequence of CD137 (4-1BB)
      intracellular region

<400> SEQUENCE: 9

Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
         35                  40

<210> SEQ ID NO 10
<211> LENGTH: 41
<212> TYPE: PRT
<213> ORGANISM: Artificial Sequence
<220> FEATURE:
<223> OTHER INFORMATION: Amino acid sequence of CD28 intracellular
      region

<400> SEQUENCE: 10

Arg Ser Lys Arg Ser Arg Leu Leu His Ser Asp Tyr Met Asn Met Thr
 1               5                  10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
         35                  40

<210> SEQ ID NO 11
<211> LENGTH: 490
<212> TYPE: PRT
<213> ORGANISM: Artificial Sequence
<220> FEATURE:
<223> OTHER INFORMATION: Amino acid sequence of CAR1

<400> SEQUENCE: 11

Met Ala Leu Pro Val Thr Ala Leu Leu Leu Pro Leu Ala Leu Leu Leu
 1               5                  10                  15

His Ala Ala Arg Pro Asp Ile Val Leu Thr Gln Ser Pro Ala Ser Leu
             20                  25                  30

Ala Val Ser Leu Gly Gln Arg Ala Thr Ile Ser Cys Arg Ala Ser Glu
         35                  40                  45

Ser Val Asp Asn Tyr Gly Asn Thr Phe Met His Trp Tyr Gln Gln Lys
     50                  55                  60

Pro Gly Gln Pro Pro Lys Leu Leu Ile Tyr Arg Ala Ser Asn Leu Glu
 65                  70                  75                  80

Ser Gly Ile Pro Ala Arg Phe Ser Gly Ser Gly Ser Arg Thr Asp Phe
             85                  90                  95
```

```
Thr Leu Thr Ile Asn Pro Val Glu Ala Asp Asp Val Ala Thr Tyr Tyr
                100                 105                 110

Cys Gln Gln Ser Asn Glu Asp Pro Pro Thr Phe Gly Ala Gly Thr Lys
            115                 120                 125

Leu Glu Leu Lys Gly Gly Gly Ser Gly Gly Gly Ser Ser Gly
        130                 135                 140

Gly Gly Ser Gln Ile Gln Leu Val Gln Ser Gly Pro Glu Leu Lys Lys
145                 150                 155                 160

Pro Gly Glu Thr Val Lys Ile Ser Cys Lys Ala Ser Gly Tyr Ile Phe
                165                 170                 175

Thr Asn Tyr Gly Met Asn Trp Val Lys Gln Ala Pro Gly Lys Ser Phe
            180                 185                 190

Lys Trp Met Gly Trp Ile Asn Thr Tyr Thr Gly Glu Ser Thr Tyr Ser
        195                 200                 205

Ala Asp Phe Lys Gly Arg Phe Ala Phe Ser Leu Glu Thr Ser Ala Ser
    210                 215                 220

Thr Ala Tyr Leu His Ile Asn Asp Leu Lys Asn Glu Asp Thr Ala Thr
225                 230                 235                 240

Tyr Phe Cys Ala Arg Ser Gly Gly Tyr Asp Pro Met Asp Tyr Trp Gly
                245                 250                 255

Gln Gly Thr Ser Val Thr Val Ser Ser Thr Ser Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
            420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

<210> SEQ ID NO 12
<211> LENGTH: 483
<212> TYPE: PRT
<213> ORGANISM: Artificial Sequence
<220> FEATURE:
<223> OTHER INFORMATION: Amino acid sequence of CAR2

<400> SEQUENCE: 12

```
Met Ala Leu Pro Val Thr Ala Leu Leu Leu Pro Leu Ala Leu Leu Leu
1               5                   10                  15

His Ala Ala Arg Pro Asp Val Gln Ile Thr Gln Ser Pro Ser Tyr Leu
            20                  25                  30

Ala Ala Ser Pro Gly Glu Thr Ile Thr Ile Asn Cys Arg Ala Ser Lys
        35                  40                  45

Ser Ile Ser Lys Asp Leu Ala Trp Tyr Gln Glu Lys Pro Gly Lys Thr
    50                  55                  60

Asn Lys Leu Leu Ile Tyr Ser Gly Ser Thr Leu Gln Ser Gly Ile Pro
65                  70                  75                  80

Ser Arg Phe Ser Gly Ser Gly Ser Gly Thr Asp Phe Thr Leu Thr Ile
                85                  90                  95

Ser Ser Leu Glu Pro Glu Asp Phe Ala Met Tyr Tyr Cys Gln Gln His
            100                 105                 110

Asn Lys Tyr Pro Tyr Thr Phe Gly Gly Gly Thr Lys Leu Glu Ile Lys
        115                 120                 125

Gly Gly Gly Gly Ser Gly Gly Gly Ser Gly Gly Gly Gly Ser Gln
    130                 135                 140

Val Gln Leu Gln Gln Pro Gly Ala Glu Leu Val Arg Pro Gly Ala Ser
145                 150                 155                 160

Val Lys Leu Ser Cys Lys Ala Ser Gly Tyr Thr Phe Thr Ser Tyr Trp
                165                 170                 175

Met Asn Trp Val Lys Gln Arg Pro Asp Gln Gly Leu Glu Trp Ile Gly
            180                 185                 190

Arg Ile Asp Pro Tyr Asp Ser Glu Thr His Tyr Asn Gln Lys Phe Lys
        195                 200                 205

Asp Lys Ala Ile Leu Thr Val Asp Lys Ser Ser Thr Ala Tyr Met
    210                 215                 220

Gln Leu Ser Ser Leu Thr Ser Glu Asp Ser Ala Val Tyr Tyr Cys Ala
225                 230                 235                 240

Arg Gly Asn Trp Asp Asp Tyr Trp Gly Gln Gly Thr Thr Leu Thr Val
                245                 250                 255

Ser Ser Thr Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
        355                 360                 365
```

```
Cys Glu Leu Arg Val Lys Phe Ser Arg Ser Ala Asp Ala Pro Ala Tyr
370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Arg Gly Arg Asp Pro Glu Met
                405                 410                 415
Gly Gly Lys Pro Arg Arg Lys Asn Pro Gln Glu Gly Leu Tyr Asn Glu
                420                 425                 430
Leu Gln Lys Asp Lys Met Ala Glu Ala Tyr Ser Glu Ile Gly Met Lys
                435                 440                 445
Gly Glu Arg Arg Arg Gly Lys Gly His Asp Gly Leu Tyr Gln Gly Leu
450                 455                 460
Ser Thr Ala Thr Lys Asp Thr Tyr Asp Ala Leu His Met Gln Ala Leu
465                 470                 475                 480
Pro Pro Arg

<210> SEQ ID NO 13
<211> LENGTH: 501
<212> TYPE: PRT
<213> ORGANISM: Artificial Sequence
<220> FEATURE:
<223> OTHER INFORMATION: Amino acid sequence of CAR3

<400> SEQUENCE: 13

Met Ala Leu Pro Val Thr Ala Leu Leu Leu Pro Leu Ala Leu Leu Leu
1               5                   10                  15
His Ala Ala Arg Pro Met Ala Asp Tyr Lys Asp Ile Val Met Thr Gln
                20                  25                  30
Ser His Lys Phe Met Ser Thr Ser Val Gly Asp Arg Val Asn Ile Thr
            35                  40                  45
Cys Lys Ala Ser Gln Asn Val Asp Ser Ala Val Ala Trp Tyr Gln Gln
        50                  55                  60
Lys Pro Gly Gln Ser Pro Lys Ala Leu Ile Tyr Ser Ala Ser Tyr Arg
65                  70                  75                  80
Tyr Ser Gly Val Pro Asp Arg Phe Thr Gly Arg Gly Ser Gly Thr Asp
                85                  90                  95
Phe Thr Leu Thr Ile Ser Ser Val Gln Ala Glu Asp Leu Ala Val Tyr
            100                 105                 110
Tyr Cys Gln Gln Tyr Tyr Ser Thr Pro Trp Thr Phe Gly Gly Gly Thr
        115                 120                 125
Lys Leu Glu Ile Lys Arg Gly Gly Gly Gly Ser Gly Gly Gly Gly Ser
130                 135                 140
Gly Gly Gly Gly Ser Glu Val Lys Leu Val Glu Ser Gly Gly Gly Leu
145                 150                 155                 160
Val Gln Pro Gly Gly Ser Leu Ser Leu Ser Cys Ala Ala Ser Gly Phe
                165                 170                 175
Thr Phe Thr Asp Tyr Tyr Met Ser Trp Val Arg Gln Pro Pro Gly Lys
            180                 185                 190
Ala Leu Glu Trp Leu Ala Leu Ile Arg Ser Lys Ala Asp Gly Tyr Thr
        195                 200                 205
Thr Glu Tyr Ser Ala Ser Val Lys Gly Arg Phe Thr Leu Ser Arg Asp
210                 215                 220
Asp Ser Gln Ser Ile Leu Tyr Leu Gln Met Asn Ala Leu Arg Pro Glu
225                 230                 235                 240
```

```
Asp Ser Ala Thr Tyr Tyr Cys Ala Arg Asp Ala Ala Tyr Tyr Ser Tyr
                    245                 250                 255

Tyr Ser Pro Glu Gly Ala Met Asp Tyr Trp Gly Gln Gly Thr Ser Val
            260                 265                 270

Thr Val Ser Ser Thr Ser Thr Thr Thr Pro Ala Pro Arg Pro Pro Thr
        275                 280                 285

Pro Ala Pro Thr Ile Ala Ser Gln Pro Leu Ser Leu Arg Pro Glu Ala
    290                 295                 300

Cys Arg Pro Ala Ala Gly Gly Ala Val His Thr Arg Gly Leu Asp Phe
305                 310                 315                 320

Ala Cys Asp Ile Tyr Ile Trp Ala Pro Leu Ala Gly Thr Cys Gly Val
                325                 330                 335

Leu Leu Leu Ser Leu Val Ile Thr Leu Tyr Cys Lys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
    370                 375                 380

Gly Gly Cys Glu Leu Arg Val Lys Phe Ser Arg Ser Ala Asp Ala Pro
385                 390                 395                 400

Ala Tyr Gln Gln Gly Gln Asn Gln Leu Tyr Asn Glu Leu Asn Leu Gly
                405                 410                 415

Arg Arg Glu Glu Tyr Asp Val Leu Asp Lys Arg Arg Gly Arg Asp Pro
            420                 425                 430

Glu Met Gly Gly Lys Pro Arg Arg Lys Asn Pro Gln Glu Gly Leu Tyr
        435                 440                 445

Asn Glu Leu Gln Lys Asp Lys Met Ala Glu Ala Tyr Ser Glu Ile Gly
    450                 455                 460

Met Lys Gly Glu Arg Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
                485                 490                 495

Ala Leu Pro Pro Arg
            500

<210> SEQ ID NO 14
<211> LENGTH: 377
<212> TYPE: PRT
<213> ORGANISM: Artificial Sequence
<220> FEATURE:
<223> OTHER INFORMATION: Amino acid sequence of CRL1

<400> SEQUENCE: 14

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95
```

```
Leu Lys Asn Leu Leu Pro Cys Leu Pro Leu Ala Thr Ala Ala Pro Thr
             100                 105                 110

Arg His Pro Ile His Ile Lys Asp Gly Asp Trp Asn Glu Phe Arg Arg
            115                 120                 125

Lys Leu Thr Phe Tyr Leu Lys Thr Leu Glu Asn Ala Gln Ala Gln Gln
        130                 135                 140

Thr Thr Leu Ser Leu Ala Ile Phe Thr Ser Thr Thr Pro Ala Pro
145                 150                 155                 160

Arg Pro Pro Thr Pro Ala Pro Thr Ile Ala Ser Gln Pro Leu Ser Leu
                165                 170                 175

Arg Pro Glu Ala Cys Arg Pro Ala Ala Gly Gly Ala Val His Thr Arg
            180                 185                 190

Gly Leu Asp Phe Ala Cys Asp Ile Tyr Ile Trp Ala Pro Leu Ala Gly
        195                 200                 205

Thr Cys Gly Val Leu Leu Ser Leu Val Ile Thr Leu Tyr Cys Lys
210                 215                 220

Arg Gly Arg Lys Lys Leu Leu Tyr Ile Phe Lys Gln Pro Phe Met Arg
225                 230                 235                 240

Pro Val Gln Thr Thr Gln Glu Glu Asp Gly Cys Ser Cys Arg Phe Pro
                245                 250                 255

Glu Glu Glu Glu Gly Gly Cys Glu Leu Arg Val Lys Phe Ser Arg Ser
            260                 265                 270

Ala Asp Ala Pro Ala Tyr Gln Gln Gly Gln Asn Gln Leu Tyr Asn Glu
        275                 280                 285

Leu Asn Leu Gly Arg Arg Glu Glu Tyr Asp Val Leu Asp Lys Arg Arg
290                 295                 300

Gly Arg Asp Pro Glu Met Gly Gly Lys Pro Arg Arg Lys Asn Pro Gln
305                 310                 315                 320

Glu Gly Leu Tyr Asn Glu Leu Gln Lys Asp Lys Met Ala Glu Ala Tyr
                325                 330                 335

Ser Glu Ile Gly Met Lys Gly Glu Arg Arg Arg Gly Lys Gly His Asp
            340                 345                 350

Gly Leu Tyr Gln Gly Leu Ser Thr Ala Thr Lys Asp Thr Tyr Asp Ala
        355                 360                 365

Leu His Met Gln Ala Leu Pro Pro Arg
370                 375

<210> SEQ ID NO 15
<211> LENGTH: 352
<212> TYPE: PRT
<213> ORGANISM: Artificial Sequence
<220> FEATURE:
<223> OTHER INFORMATION: Amino acid sequence of CRL2

<400> SEQUENCE: 15

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80
```

```
Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe Thr Ser Thr Thr Pro Ala Pro
145                 150                 155                 160

Arg Pro Pro Thr Pro Ala Pro Thr Ile Ala Ser Gln Pro Leu Ser Leu
                165                 170                 175

Arg Pro Glu Ala Cys Arg Pro Ala Ala Gly Gly Ala Val His Thr Arg
            180                 185                 190

Gly Leu Asp Phe Ala Cys Asp Arg Ser Lys Arg Ser Arg Leu Leu His
        195                 200                 205

Ser Asp Tyr Met Asn Met Thr Pro Arg Pro Gly Pro Thr Arg Lys
    210                 215                 220

His Tyr Gln Pro Tyr Ala Pro Pro Arg Asp Phe Ala Ala Tyr Arg Ser
225                 230                 235                 240

Arg Val Lys Phe Ser Arg Ser Ala Asp Ala Pro Ala Tyr Gln Gln Gly
                245                 250                 255

Gln Asn Gln Leu Tyr Asn Glu Leu Asn Leu Gly Arg Arg Glu Glu Tyr
            260                 265                 270

Asp Val Leu Asp Lys Arg Arg Gly Arg Asp Pro Glu Met Gly Gly Lys
        275                 280                 285

Pro Arg Arg Lys Asn Pro Gln Glu Gly Leu Tyr Asn Glu Leu Gln Lys
    290                 295                 300

Asp Lys Met Ala Glu Ala Tyr Ser Glu Ile Gly Met Lys Gly Glu Arg
305                 310                 315                 320

Arg Arg Gly Lys Gly His Asp Gly Leu Tyr Gln Gly Leu Ser Thr Ala
                325                 330                 335

Thr Lys Asp Thr Tyr Asp Ala Leu His Met Gln Ala Leu Pro Pro Arg
            340                 345                 350

<210> SEQ ID NO 16
<211> LENGTH: 418
<212> TYPE: PRT
<213> ORGANISM: Artificial Sequence
<220> FEATURE:
<223> OTHER INFORMATION: Amino acid sequence of CRL3

<400> SEQUENCE: 16

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95
```

```
Leu Lys Asn Leu Leu Pro Cys Leu Pro Leu Ala Thr Ala Ala Pro Thr
             100                 105                 110

Arg His Pro Ile His Ile Lys Asp Gly Asp Trp Asn Glu Phe Arg Arg
         115                 120                 125

Lys Leu Thr Phe Tyr Leu Lys Thr Leu Glu Asn Ala Gln Ala Gln Gln
     130                 135                 140

Thr Thr Leu Ser Leu Ala Ile Phe Thr Ser Thr Thr Pro Ala Pro
145                 150                 155                 160

Arg Pro Pro Thr Pro Ala Pro Thr Ile Ala Ser Gln Pro Leu Ser Leu
                 165                 170                 175

Arg Pro Glu Ala Cys Arg Pro Ala Ala Gly Gly Ala Val His Thr Arg
             180                 185                 190

Gly Leu Asp Phe Ala Cys Asp Arg Ser Lys Arg Ser Arg Leu Leu His
         195                 200                 205

Ser Asp Tyr Met Asn Met Thr Pro Arg Arg Pro Gly Pro Thr Arg Lys
210                 215                 220

His Tyr Gln Pro Tyr Ala Pro Pro Arg Asp Phe Ala Ala Tyr Arg Ser
225                 230                 235                 240

Ile Tyr Ile Trp Ala Pro Leu Ala Gly Thr Cys Gly Val Leu Leu Leu
                 245                 250                 255

Ser Leu Val Ile Thr Leu Tyr Cys Lys Arg Gly Arg Lys Lys Leu Leu
             260                 265                 270

Tyr Ile Phe Lys Gln Pro Phe Met Arg Pro Val Gln Thr Thr Gln Glu
         275                 280                 285

Glu Asp Gly Cys Ser Cys Arg Phe Pro Glu Glu Glu Glu Gly Gly Cys
     290                 295                 300

Glu Leu Arg Val Lys Phe Ser Arg Ser Ala Asp Ala Pro Ala Tyr Gln
305                 310                 315                 320

Gln Gly Gln Asn Gln Leu Tyr Asn Glu Leu Asn Leu Gly Arg Arg Glu
                 325                 330                 335

Glu Tyr Asp Val Leu Asp Lys Arg Arg Gly Arg Asp Pro Glu Met Gly
             340                 345                 350

Gly Lys Pro Arg Arg Lys Asn Pro Gln Glu Gly Leu Tyr Asn Glu Leu
         355                 360                 365

Gln Lys Asp Lys Met Ala Glu Ala Tyr Ser Glu Ile Gly Met Lys Gly
     370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                 405                 410                 415

Pro Arg

<210> SEQ ID NO 17
<211> LENGTH: 379
<212> TYPE: PRT
<213> ORGANISM: Artificial Sequence
<220> FEATURE:
<223> OTHER INFORMATION: Amino acid sequence of CRL4

<400> SEQUENCE: 17

Met Ala Leu Pro Val Thr Ala Leu Leu Leu Pro Leu Ala Leu Leu Leu
1               5                   10                  15

His Ala Ala Arg Pro Ala Pro Met Thr Gln Thr Thr Pro Leu Lys Thr
             20                  25                  30
```

```
Ser Trp Val Asn Cys Ser Asn Met Ile Asp Glu Ile Ile Thr His Leu
         35                  40                  45

Lys Gln Pro Pro Leu Pro Leu Leu Asp Phe Asn Asn Leu Asn Gly Glu
 50                  55                  60

Asp Gln Asp Ile Leu Met Glu Asn Asn Leu Arg Arg Pro Asn Leu Glu
 65                  70                  75                  80

Ala Phe Asn Arg Ala Val Lys Ser Leu Gln Asn Ala Ser Ala Ile Glu
                 85                  90                  95

Ser Ile Leu Lys Asn Leu Leu Pro Cys Leu Pro Leu Ala Thr Ala Ala
                100                 105                 110

Pro Thr Arg His Pro Ile His Ile Lys Asp Gly Asp Trp Asn Glu Phe
                115                 120                 125

Arg Arg Lys Leu Thr Phe Tyr Leu Lys Thr Leu Glu Asn Ala Gln Ala
            130                 135                 140

Gln Gln Thr Thr Leu Ser Leu Ala Ile Phe Thr Ser Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
                180                 185                 190

Thr Arg Gly Leu Asp Phe Ala Cys Asp Ile Tyr Ile Trp Ala Pro Leu
            195                 200                 205

Ala Gly Thr Cys Gly Val Leu Leu Ser Leu Val Ile Thr Leu Tyr
210                 215                 220

Cys Lys Arg Gly Arg Lys Lys Leu Leu Tyr Ile Phe Lys Gln Pro Phe
225                 230                 235                 240

Met Arg Pro Val Gln Thr Thr Gln Glu Glu Asp Gly Cys Ser Cys Arg
                245                 250                 255

Phe Pro Glu Glu Glu Glu Gly Gly Cys Glu Leu Arg Val Lys Phe Ser
                260                 265                 270

Arg Ser Ala Asp Ala Pro Ala Tyr Gln Gln Gly Gln Asn Gln Leu Tyr
            275                 280                 285

Asn Glu Leu Asn Leu Gly Arg Arg Glu Glu Tyr Asp Val Leu Asp Lys
290                 295                 300

Arg Arg Gly Arg Asp Pro Glu Met Gly Gly Lys Pro Arg Arg Lys Asn
305                 310                 315                 320

Pro Gln Glu Gly Leu Tyr Asn Glu Leu Gln Lys Asp Lys Met Ala Glu
                325                 330                 335

Ala Tyr Ser Glu Ile Gly Met Lys Gly Glu Arg Arg Arg Gly Lys Gly
            340                 345                 350

His Asp Gly Leu Tyr Gln Gly Leu Ser Thr Ala Thr Lys Asp Thr Tyr
            355                 360                 365

Asp Ala Leu His Met Gln Ala Leu Pro Pro Arg
            370                 375

<210> SEQ ID NO 18
<211> LENGTH: 354
<212> TYPE: PRT
<213> ORGANISM: Artificial Sequence
<220> FEATURE:
<223> OTHER INFORMATION: Amino acid sequence of CRL5
```

<400> SEQUENCE: 18

```
Met Ala Leu Pro Val Thr Ala Leu Leu Pro Leu Ala Leu Leu Leu
1               5                   10                  15

His Ala Ala Arg Pro Ala Pro Met Thr Gln Thr Thr Pro Leu Lys Thr
            20                  25                  30

Ser Trp Val Asn Cys Ser Asn Met Ile Asp Glu Ile Thr His Leu
        35                  40                  45

Lys Gln Pro Pro Leu Pro Leu Leu Asp Phe Asn Asn Leu Asn Gly Glu
    50                  55                  60

Asp Gln Asp Ile Leu Met Glu Asn Asn Leu Arg Arg Pro Asn Leu Glu
65                  70                  75                  80

Ala Phe Asn Arg Ala Val Lys Ser Leu Gln Asn Ala Ser Ala Ile Glu
                85                  90                  95

Ser Ile Leu Lys Asn Leu Leu Pro Cys Leu Pro Leu Ala Thr Ala Ala
            100                 105                 110

Pro Thr Arg His Pro Ile His Ile Lys Asp Gly Asp Trp Asn Glu Phe
            115                 120                 125

Arg Arg Lys Leu Thr Phe Tyr Leu Lys Thr Leu Glu Asn Ala Gln Ala
130                 135                 140

Gln Gln Thr Thr Leu Ser Leu Ala Ile Phe Thr Ser Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Arg Ser Lys Arg Ser Arg Leu
            195                 200                 205

Leu His Ser Asp Tyr Met Asn Met Thr Pro Arg Arg Pro Gly Pro Thr
            210                 215                 220

Arg Lys His Tyr Gln Pro Tyr Ala Pro Pro Arg Asp Phe Ala Ala Tyr
225                 230                 235                 240

Arg Ser Arg Val Lys Phe Ser Arg Ser Ala Asp Ala Pro Ala Tyr Gln
                245                 250                 255

Gln Gly Gln Asn Gln Leu Tyr Asn Glu Leu Asn Leu Gly Arg Arg Glu
            260                 265                 270

Glu Tyr Asp Val Leu Asp Lys Arg Arg Gly Arg Asp Pro Glu Met Gly
            275                 280                 285

Gly Lys Pro Arg Arg Lys Asn Pro Gln Glu Gly Leu Tyr Asn Glu Leu
            290                 295                 300

Gln Lys Asp Lys Met Ala Glu Ala Tyr Ser Glu Ile Gly Met Lys Gly
305                 310                 315                 320

Glu Arg Arg Arg Gly Lys Gly His Asp Gly Leu Tyr Gln Gly Leu Ser
                325                 330                 335

Thr Ala Thr Lys Asp Thr Tyr Asp Ala Leu His Met Gln Ala Leu Pro
            340                 345                 350

Pro Arg
```

<210> SEQ ID NO 19
<211> LENGTH: 420
<212> TYPE: PRT
<213> ORGANISM: Artificial Sequence
<220> FEATURE:
<223> OTHER INFORMATION: Amino acid sequence of CRL6

<400> SEQUENCE: 19

```
Met Ala Leu Pro Val Thr Ala Leu Leu Leu Pro Leu Ala Leu Leu Leu
1               5                   10                  15

His Ala Ala Arg Pro Ala Pro Met Thr Gln Thr Thr Pro Leu Lys Thr
            20                  25                  30

Ser Trp Val Asn Cys Ser Asn Met Ile Asp Glu Ile Thr His Leu
        35                  40                  45

Lys Gln Pro Pro Leu Pro Leu Leu Asp Phe Asn Asn Leu Asn Gly Glu
    50                  55                  60

Asp Gln Asp Ile Leu Met Glu Asn Asn Leu Arg Arg Pro Asn Leu Glu
65                  70                  75                  80

Ala Phe Asn Arg Ala Val Lys Ser Leu Gln Asn Ala Ser Ala Ile Glu
                85                  90                  95

Ser Ile Leu Lys Asn Leu Leu Pro Cys Leu Pro Leu Ala Thr Ala Ala
            100                 105                 110

Pro Thr Arg His Pro Ile His Ile Lys Asp Gly Asp Trp Asn Glu Phe
        115                 120                 125

Arg Arg Lys Leu Thr Phe Tyr Leu Lys Thr Leu Glu Asn Ala Gln Ala
    130                 135                 140

Gln Gln Thr Thr Leu Ser Leu Ala Ile Phe Thr Ser Thr Thr Pro
145                 150                 155                 160

Ala Pro Arg Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Arg Ser Lys Arg Ser Arg Leu
        195                 200                 205

Leu His Ser Asp Tyr Met Asn Met Thr Pro Arg Arg Pro Gly Pro Thr
    210                 215                 220

Arg Lys His Tyr Gln Pro Tyr Ala Pro Pro Arg Asp Phe Ala Ala Tyr
225                 230                 235                 240

Arg Ser Ile Tyr Ile Trp Ala Pro Leu Ala Gly Thr Cys Gly Val Leu
                245                 250                 255

Leu Leu Ser Leu Val Ile Thr Leu Tyr Cys Lys Arg Gly Arg Lys Lys
            260                 265                 270

Leu Leu Tyr Ile Phe Lys Gln Pro Phe Met Arg Pro Val Gln Thr Thr
        275                 280                 285

Gln Glu Glu Asp Gly Cys Ser Cys Arg Phe Pro Glu Glu Glu Glu Gly
    290                 295                 300

Gly Cys Glu Leu Arg Val Lys Phe Ser Arg Ser Ala Asp Ala Pro Ala
305                 310                 315                 320

Tyr Gln Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
            340                 345                 350

Met Gly Gly Lys Pro Arg Arg Lys Asn Pro Gln Glu Gly Leu Tyr Asn
        355                 360                 365

Glu Leu Gln Lys Asp Lys Met Ala Glu Ala Tyr Ser Glu Ile Gly Met
    370                 375                 380

Lys Gly Glu Arg Arg Arg Gly Lys Gly His Asp Gly Leu Tyr Gln Gly
385                 390                 395                 400
```

Leu Ser Thr Ala Thr Lys Asp Thr Tyr Asp Ala Leu His Met Gln Ala
            405                 410                 415

Leu Pro Pro Arg
            420

<210> SEQ ID NO 20
<211> LENGTH: 399
<212> TYPE: DNA
<213> ORGANISM: Artificial Sequence
<220> FEATURE:
<223> OTHER INFORMATION: Nucleotide sequence of IL-3 receptor binding
      domain

<400> SEQUENCE: 20
gccccaatga cacagacaac cccactgaaa acctcttggg tgaactgcag caatatgatc      60
gacgagatca tcacacacct gaagcagccc cctctgcccc tgctggattt caacaatctg     120
aacggcgagg accaggatat cctgatggag aacaatctga cggcccaa cctggaggcc      180 tttaatcggg ccgtgaagag cctgcagaac gccagcgcca tcgagtccat cctgaagaat     240
ctgctgccat gtctgccact ggcaaccgca gcacctacaa ggcacccaat ccacatcaag     300
gacggcgatt ggaatgagtt caggcgcaag ctgacctttt acctgaaaac actggaaaac     360
gctcaggcac agcagaccac actgtcactg gcaatcttc                            399

<210> SEQ ID NO 21
<211> LENGTH: 372
<212> TYPE: DNA
<213> ORGANISM: Artificial Sequence
<220> FEATURE:
<223> OTHER INFORMATION: Nucleotide sequence of IL-3 receptor binding
      domain

<400> SEQUENCE: 21
gccccaatga cacagacaac cccactgaaa acctcttggg tgaactgcag caatatgatc      60
gacgagatca tcacacacct gaagcagccc cctctgcccc tgctggattt caacaatctg     120
aacggcgagg accaggatat cctgatggag aacaatctga cggcccaa cctggaggcc      180 tttaatcggg ccgtgaagag cctgcagaac gccagcgcca tcgagtccat cctgaagaat     240
ctgctgccat gtctgccact ggcaaccgca gcacctacaa ggcacccaat ccacatcaag     300
gacggcgatt ggaatgagtt caggcgcaag ctgacctttt acctgaaaac actggaaaac     360
gctcaggcac ag                                                         372

<210> SEQ ID NO 22
<211> LENGTH: 57
<212> TYPE: DNA
<213> ORGANISM: Artificial Sequence
<220> FEATURE:
<223> OTHER INFORMATION: Nucleotide sequence of IL-3 signal peptide

<400> SEQUENCE: 22
atgagtagac tgcccgtgct gctgctgctg cagctgctgg tgcgacctgg actgcag        57

<210> SEQ ID NO 23
<211> LENGTH: 63
<212> TYPE: DNA
<213> ORGANISM: Artificial Sequence
<220> FEATURE:
<223> OTHER INFORMATION: Nucleotide sequence of CD8 signal peptide

<400> SEQUENCE: 23

| atggccttac cagtgaccgc cttgctcctg ccgctggcct tgctgctcca cgccgccagg | 60 |
| ccg | 63 |

<210> SEQ ID NO 24
<211> LENGTH: 135
<212> TYPE: DNA
<213> ORGANISM: Artificial Sequence
<220> FEATURE:
<223> OTHER INFORMATION: Nucleotide sequence of CD8 hinge region

<400> SEQUENCE: 24

| accacgacgc cagcgccgcg accaccaaca ccggcgccca ccatcgcgtc gcagcccctg | 60 |
| tccctgcgcc cagaggcgtg ccggccagcg gcggggggcg cagtgcacac gagggggctg | 120 |
| gacttcgcct gtgat | 135 |

<210> SEQ ID NO 25
<211> LENGTH: 72
<212> TYPE: DNA
<213> ORGANISM: Artificial Sequence
<220> FEATURE:
<223> OTHER INFORMATION: Nucleotide sequence of CD8 transmembrane region

<400> SEQUENCE: 25

| atctacatct gggcgcccttgccgggact tgtggggtcc ttctcctgtc actggttatc | 60 |
| accctttact gc | 72 |

<210> SEQ ID NO 26
<211> LENGTH: 81
<212> TYPE: DNA
<213> ORGANISM: Artificial Sequence
<220> FEATURE:
<223> OTHER INFORMATION: Nucleotide sequence of CD28 transmembrane region

<400> SEQUENCE: 26

| ttcccggacc ttctaagccc ttttgggtgc tggtggtggt tggtggagtc ctggcttgct | 60 |
| atagcttgct agtaacagtg g | 81 |

<210> SEQ ID NO 27
<211> LENGTH: 336
<212> TYPE: DNA
<213> ORGANISM: Artificial Sequence
<220> FEATURE:
<223> OTHER INFORMATION: Nucleotide sequence of CD3z

<400> SEQUENCE: 27

| agagtgaagt tcagcaggag cgcagacgcc cccgcgtacc agcagggcca gaaccagctc | 60 |
| tataacgagc tcaatctagg acgaagagag gagtacgatg ttttggacaa gagacgtggc | 120 |
| cgggaccctg agatgggggg aaagccgaga aggaagaacc ctcaggaagg cctgtacaat | 180 |
| gaactgcaga agataagat ggcggaggcc tacagtgaga ttgggatgaa aggcgagcgc | 240 |
| cggagggggca aggggcacga tggcctttac cagggtctca gtacagccac caaggacacc | 300 |
| tacgacgccc ttcacatgca ggccctgccc cctcgc | 336 |

<210> SEQ ID NO 28
<211> LENGTH: 126
<212> TYPE: DNA
<213> ORGANISM: Artificial Sequence -continued
<220> FEATURE:
<223> OTHER INFORMATION: Nucleotide sequence of CD137 (4-1BB)
      intracellular region

<400> SEQUENCE: 28
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 29
<211> LENGTH: 143
<212> TYPE: DNA
<213> ORGANISM: Artificial Sequence
<220> FEATURE:
<223> OTHER INFORMATION: Nucleotide sequence of CD28 intracellular
      region

<400> SEQUENCE: 29
cctttattat tttctgggtg aggagtaaga ggagcaggct cctgcacagt gactacatga    60
acatgactcc ccgccgcccc gggcccaccc gcaagcatta ccagccctat gccccaccac   120
gcgacttcgc agcctatcgc tcc                                           143

<210> SEQ ID NO 30
<211> LENGTH: 1479
<212> TYPE: DNA
<213> ORGANISM: Artificial Sequence
<220> FEATURE:
<223> OTHER INFORMATION: Nucleotide sequence of CAR1

<400> SEQUENCE: 30
atggctctgc ccgtgaccgc actgctgctg ccctggctc tgctgctgca cgccgcccga    60
cctggaagcg acatcgtcct gacacagagc ccagcatccc tggccgtgtc cctgggacag   120
cgggccacca tctcttgcag agcctctgag agcgtggaca actacggcaa tacattcatg   180
cactggtatc agcagaagcc cggccagccc cctaagctgc tgatctaccg ggcctccaac   240
ctggagtctg gcatccccgc aaggttctcc ggatctggca ccgcaccga ctttaccctg    300 acaatcaacc ctgtggaggc cgacgatgtg gccacatact attgccagca gagcaatgag   360
gatccaccca cctttggcgc cggcacaaag ctggagctga gggaggagg aggatccgga    420 ggaggaggaa gctccggagg aggctctcag atccagctgg tgcagagcgg ccctgagctg   480
aagaagccag gcgagacagt gaagatcagc tgtaaggcct ccggctacat cttcacaaac   540
tatggcatga attgggtgaa gcaggcccct ggcaagtctt ttaagtggat gggctggatc   600
aatacctaca caggcgagtc tacctatagc gccgatttca agggccggtt cgcctttagc   660
ctggagacaa gcgcctctac agcctacctg cacatcaacg acctgaagaa tgaggatacc   720 gcccacatatt tttgtgccag gtcagggggg tatgatccta tggactattg ggggcagggg   780
acctccgtga ccgtctcaag cactagtacc acgacgccag cgccgcgacc accaacaccg   840
gcgcccacca tcgcgtcgca gccctgtcc ctgcgcccag aggcgtgccg gccagcggcg   900
gggggcgcag tgcacacgag ggggctggac ttcgcctgtg atatctacat ctgggcgccc   960
ttggccggga cttgtggggt ccttctcctg tcactggtta tcacccttta ctgcaaacgg   1020
ggcagaaaga aactcctgta tatattcaaa caaccattta tgagaccagt acaaactact   1080
caagaggaag atggctgtag ctgccgattt ccagaagaag aagaaggagg atgtgaactg   1140
agagtgaagt tcagcaggag cgcagacgcc cccgcgtacc agcagggcca gaaccagctc   1200

```
tataacgagc tcaatctagg acgaagagag gagtacgatg ttttggacaa gagacgtggc   1260
cgggaccctg agatggggggg aaagccgaga aggaagaacc ctcaggaagg cctgtacaat   1320
gaactgcaga aagataagat ggcggaggcc tacagtgaga ttgggatgaa aggcgagcgc   1380
cggaggggca aggggcacga tggcctttac cagggtctca gtacagccac caaggacacc   1440
tacgacgccc ttcacatgca ggccctgccc cctcgctaa                          1479

<210> SEQ ID NO 31
<211> LENGTH: 1452
<212> TYPE: DNA
<213> ORGANISM: Artificial Sequence
<220> FEATURE:
<223> OTHER INFORMATION: Nucleotide sequence of CAR2

<400> SEQUENCE: 31
atggccctgc ccgtcactgc cctgctgctg cccctggccc tgctgctgca cgccgcaaga     60
cccgatgtcc agattactca gagcccatcc tacctggccg cctctcccgg cgagacaatc    120
acaatcaact gcagggcctc caagtctatc agcaaggacc tggcctggta ccaggagaag    180
cccggcaaga ccaataagct gctgatctat ccggctcta cactgcagtc tggcatccct     240
agcaggttca gcggatccgg atctggaacc gactttaccc tgacaatcag ctccctggag    300
cctgaggatt tcgccatgta ctattgccag cagcacaaca gtacccata taccctttggc    360 ggcggcacaa agctggagat caaggggagga ggaggaagcg gaggaggagg atccggcggc    420
ggcggctctc aggtgcagct gcagcagccc ggcgccgagc tggtgcggcc tggagcatcc    480
gtgaagctgt cttgtaaggc cagcggctac accttcacat cctattggat gaactggggtg    540 aagcagcggc cagaccaggg cctggagtgg atcggcagaa tcgacccta cgatagcgag    600 acacactata atcagaagtt taaggacaag gccatcctga ccgtggataa gtctagctcc    660
acagcctata tgcagctgtc tagcctgaca agcgaggatt ccgccgtgta ctattgtgct    720
cggggaaact gggatgacta ttggggacag gggacaactc tgaccgtctc aagcactagt    780
accacgacgc cagcgccgcg accaccaaca ccggcgccca ccatcgcgtc gcagcccctg    840
tccctgcgcc cagaggcgtg ccggccagcg cggggggcgc agtgcacac gaggggggctg    900 gacttcgcct gtgatatcta catctgggcg cccttggccg ggacttgtgg ggtccttctc    960
ctgtcactgg ttatcaccct ttactgcaaa cggggcagaa agaaactcct gtatatattc   1020
aaacaaccat ttatgagacc agtacaaact actcaagagg aagatggctg tagctgccga   1080
tttccagaag aagaagaagg aggatgtgaa ctgagagtga agttcagcag gagcgcagac   1140 gccccccgcgt accagcaggg ccagaaccag ctctataacg agctcaatct aggacgaaga   1200
gaggagtacg atgttttggga caagagacgt ggccgggacc ctgagatggg gggaaagccg   1260
agaaggaaga accctcagga aggcctgtac aatgaactgc agaaagataa gatggcggag    1320
gcctacagtg agattgggat gaaaggcgag cgccggaggg gcaaggggca cgatggcctt    1380
taccagggtc tcagtacagc caccaaggac acctacgacg cccttcacat gcaggccctg    1440
ccccctcgct aa                                                         1452

<210> SEQ ID NO 32
<211> LENGTH: 1509
<212> TYPE: DNA
<213> ORGANISM: Artificial Sequence
<220> FEATURE:
<223> OTHER INFORMATION: Nucleotide sequence of CAR3
```

<400> SEQUENCE: 32

```
atggctctgc ctgtgaccgc actgctgctg cccctggctc tgctgctgca cgctgcccgc      60
cctatggccg actataaaga cattgtgatg acccagtctc acaagttcat gtctacaagc     120
gtgggcgacc gggtgaacat cacctgcaag gcctcccaga tgtggattc tgccgtggcc      180
tggtaccagc agaagccagg ccagtccccc aaggccctga tctattccgc tcttaccgg      240
tattctggag tgcctgacag gttcaccgga gaggaagcg gcacagattt taccctgaca      300
atcagctccg tgcaggcaga ggacctggca gtgtactatt gccagcagta ctatagcacc     360
ccatggacat ttggcggcgg caccaagctg gagatcaaga ggggaggagg aggaagcgga     420
ggaggaggat ccggcggcgg cggctctgag gtgaagctgg tggagtccgg aggaggcctg     480
gtgcagccag gaggcagcct gtccctgtct tgtgccgcca gcggcttcac ctttacagac     540
tactatatgt cctgggtcag gcagccacct ggaaaggcac tggagtggct ggcactgatc     600
aggagcaagg ccgatggcta caccacagag atatagcgcct ccgtgaaggg caggttcacc     660
ctgtcccgcg acgattctca gagcatcctg tacctgcaga tgaacgcact gcggcctgag     720
gactccgcaa catactattg tgccagagat gccgcctact attcttacta ttcaccagaa     780
ggggctatgg attattgggg cagggggaca agcgtcaccg tctcatcatc aactagtacc     840
acgacgccag cgccgcgacc accaacaccg gcgcccacca tcgcgtcgca gcccctgtcc     900
ctgcgcccag aggcgtgccg gccagcggcg ggggcgcag tgcacacgag ggggctggac     960
ttcgcctgtg atatctacat ctgggcgccc ttggccggga cttgtggggt ccttctcctg    1020
tcactggtta tcacccttta ctgcaaacgg gcagaaaga aactcctgta tatattcaaa    1080
caaccattta tgagaccagt acaaactact caagaggaag atggctgtag ctgccgatt    1140
ccagaagaag aagaaggagg atgtgaactg agagtgaagt tcagcaggag cgcagacgcc    1200
cccgcgtacc agcagggcca gaaccagctc tataacgagc tcaatctagg acgaagagag    1260
gagtacgatg ttttggacaa gagacgtggc cgggaccctg agatggggg aaagccgaga    1320
aggaagaacc ctcaggaagg cctgtacaat gaactgcaga agataagat ggcggaggcc    1380
tacagtgaga ttgggatgaa aggcgagcgc cggagggca aggggcacga tggcctttac    1440
cagggtctca gtacagccac caaggacacc tacgacgccc ttcacatgca ggccctgccc    1500
cctcgctaa                                                            1509
```

<210> SEQ ID NO 33
<211> LENGTH: 1134
<212> TYPE: DNA
<213> ORGANISM: Artificial Sequence
<220> FEATURE:
<223> OTHER INFORMATION: Nucleotide sequence of CRL1

<400> SEQUENCE: 33

```
atgagtagac tgcccgtgct gctgctgctg cagctgctgg tgcgacctgg actgcaggcc      60
ccaatgacac agacaacccc actgaaaacc tcttgggtga actgcagcaa tatgatcgac     120
gagatcatca cacacctgaa gcagccccct ctgcccctgc tggatttcaa caatctgaac     180
ggcgaggacc aggatatcct gatggagaac aatctgagac ggcccaacct ggaggccttt     240
aatcgggccg tgaagagcct gcagaacgcc agcgccatcg agtccatcct gaagaatctg     300
ctgccatgtc tgccactggc aaccgcagca cctacaaggc acccaatcca catcaaggac     360
ggcgattgga atgagttcag gcgcaagctg acctttttacc tgaaaacact ggaaaacgct     420
caggcacagc agaccacact gtcactggca atcttcacta gtaccacgac gccagcgccg     480
```

| | |
|---|---|
| cgaccaccaa caccggcgcc caccatcgcg tcgcagcccc tgtccctgcg cccagaggcg | 540 |
| tgccggccag cggcggggg cgcagtgcac acgagggggc tggacttcgc ctgtgatatc | 600 |
| tacatctggg cgcccttggc cgggacttgt ggggtccttc tcctgtcact ggttatcacc | 660 |
| ctttactgca aacggggcag aaagaaactc ctgtatatat tcaaacaacc atttatgaga | 720 |
| ccagtacaaa ctactcaaga ggaagatggc tgtagctgcc gatttccaga agaagaagaa | 780 |
| ggaggatgtg aactgagagt gaagttcagc aggagcgcag acgccccgc gtaccagcag | 840 |
| ggccagaacc agctctataa cgagctcaat ctaggacgaa gagaggagta cgatgttttg | 900 |
| gacaagagac gtggccggga ccctgagatg ggggaaagc cgagaaggaa gaaccctcag | 960 |
| gaaggcctgt acaatgaact gcagaaagat aagatggcgg aggcctacag tgagattggg | 1020 |
| atgaaaggcg agcgccggag gggcaagggg cacgatggcc tttaccaggg tctcagtaca | 1080 |
| gccaccaagg acacctacga cgcccttcac atgcaggccc tgccccctcg ctaa | 1134 |

<210> SEQ ID NO 34
<211> LENGTH: 1151
<212> TYPE: DNA
<213> ORGANISM: Artificial Sequence
<220> FEATURE:
<223> OTHER INFORMATION: Nucleotide sequence of CRL2

<400> SEQUENCE: 34

| | |
|---|---|
| atgagtagac tgcccgtgct gctgctgctg cagctgctgg tgcgacctgg actgcaggcc | 60 |
| ccaatgacac agacaacccc actgaaaacc tcttgggtga actgcagcaa tatgatcgac | 120 |
| gagatcatca cacacctgaa gcagcccct ctgcccctgc tggatttcaa caatctgaac | 180 |
| ggcgaggacc aggatatcct gatggagaac aatctgagac ggcccaacct ggaggccttt | 240 |
| aatcgggccg tgaagagcct gcagaacgcc agcgccatcg agtccatcct gaagaatctg | 300 |
| ctgccatgtc tgccactggc aaccgcagca cctacaaggc acccaatcca catcaaggac | 360 |
| ggcgattgga atgagttcag cgcgcaagctg accttttacc tgaaaacact ggaaaacgct | 420 |
| caggcacagc agaccacact gtcactggca atcttcacta gtaccacgac gccagcgccg | 480 |
| cgaccaccaa caccggcgcc caccatcgcg tcgcagcccc tgtccctgcg cccagaggcg | 540 |
| tgccggccag cggcggggg cgcagtgcac acgagggggc tggacttcgc ctgtgatatc | 600 |
| tacatctggg cgcccttggc cgggacttgt ggggtccttc tcctgtcact ggttatcacc | 660 |
| ctttactgcc ctttattatt ttctgggtga ggagtaagag gagcaggctc ctgcacagtg | 720 |
| actacatgaa catgactccc cgccgccccg ggcccacccg caagcattac cagcccctatg | 780 |
| ccccaccacg cgacttcgca gcctatcgct ccagagtgaa gttcagcagg agcgcagacg | 840 |
| cccccgcgta ccagcagggc cagaaccagc tctataacga gctcaatcta ggacgaagag | 900 |
| aggagtacga tgttttggac aagagacgtg gccgggaccc tgagatgggg ggaaagccga | 960 |
| gaaggaagaa ccctcaggaa ggcctgtaca atgaactgca gaaagataag atggcggagg | 1020 |
| cctacagtga gattgggatg aaaggcgagc gccggagggg caaggggcac gatggccttt | 1080 |
| accagggtct cagtacagcc accaaggaca cctacgacgc ccttcacatg caggccctgc | 1140 |
| cccctcgcta a | 1151 |

<210> SEQ ID NO 35
<211> LENGTH: 1277
<212> TYPE: DNA
<213> ORGANISM: Artificial Sequence
<220> FEATURE:
<223> OTHER INFORMATION: Nucleotide sequence of CRL3

```
<400> SEQUENCE: 35
atgagtagac tgcccgtgct gctgctgctg cagctgctgg tgcgacctgg actgcaggcc      60
ccaatgacac agacaacccc actgaaaacc tcttgggtga actgcagcaa tatgatcgac     120
gagatcatca cacacctgaa gcagccccct ctgcccctgc tggatttcaa caatctgaac     180
ggcgaggacc aggatatcct gatggagaac aatctgagac ggcccaacct ggaggccttt     240
aatcgggccg tgaagagcct gcagaacgcc agcgccatcg agtccatcct gaagaatctg     300
ctgccatgtc tgccactggc aaccgcagca cctacaaggc acccaatcca catcaaggac     360
ggcgattgga atgagttcag gcgcaagctg accttttacc tgaaaacact ggaaaacgct     420
caggcacagc agaccacact gtcactggca atcttcacta gtaccacgac gccagcgccg     480
cgaccaccaa caccggcgcc caccatcgcg tcgcagcccc tgtccctgcg cccagaggcg     540
tgccggccag cggcggggcg cgcagtgcac acgagggggc tggacttcgc ctgtgatatc     600
tacatctggg cgcccttggc cgggacttgt ggggtccttc tcctgtcact ggttatcacc     660
ctttactgcc ctttattatt ttctgggtga ggagtaagag gagcaggctc ctgcacagtg     720
actacatgaa catgactccc cgccgccccg ggcccacccg caagcattac cagccctatg     780
ccccaccacg cgacttcgca gcctatcgct ccaaacgggg cagaaagaaa ctcctgtata     840
tattcaaaca accatttatg agaccagtac aaactactca agaggaagat ggctgtagct     900
gccgatttcc agaagaagaa gaggaggat gtgaactgag agtgaagttc agcaggagcg     960
cagacgcccc cgcgtaccag cagggccaga accagctcta taacgagctc aatctaggac    1020
gaagagagga gtacgatgtt ttggacaaga gacgtggccg ggaccctgag atgggggaa     1080 agccgagaag gaagaaccct caggaaggcc tgtacaatga actgcagaaa gataagatgg    1140
cggaggccta cagtgagatt gggatgaaag gcgagcgccg gaggggcaag gggcacgatg    1200
gcctttacca gggtctcagt acagccacca aggacaccta cgacgccctt cacatgcagg    1260
ccctgccccc tcgctaa                                                  1277

<210> SEQ ID NO 36
<211> LENGTH: 1140
<212> TYPE: DNA
<213> ORGANISM: Artificial Sequence
<220> FEATURE:
<223> OTHER INFORMATION: Nucleotide sequence of CRL4

<400> SEQUENCE: 36
atggccttac cagtgaccgc cttgctcctg ccgctggcct tgctgctcca cgccgccagg      60
ccggccccaa tgacacagac aaccccactg aaaacctctt gggtgaactg cagcaatatg     120
atcgacgaga tcatcacaca cctgaagcag ccccctctgc ccctgctgga tttcaacaat     180
ctgaacggcg aggaccagga tatcctgatg gagaacaatc tgagacggcc caacctggag     240
gcctttaatc gggccgtgaa gagcctgcag aacgccagcg ccatcgagtc catcctgaag     300
aatctgctgc catgtctgcc actggcaacc gcagcaccta caaggcaccc aatccacatc     360
aaggacggcg attggaatga gttcaggcgc aagctgacct tttacctgaa aacactggaa     420
aacgctcagg cacagcagac cacactgtca ctggcaatct tcactagtac cacgacgcca     480
gcgccgcgac caccaacacc ggcgcccacc atcgcgtcgc agcccctgtc cctgcgccca     540
gaggcgtgcc ggccagcggc ggggcgcgca gtgcacacga ggggctgga cttcgcctgt     600 gatatctaca tctgggcgcc cttggccggg acttgtgggg tccttctcct gtcactggtt     660
atcacccttt actgcaaacg gggcagaaag aaactcctgt atatattcaa acaaccattt     720
```

| | |
|---|---|
| atgagaccag tacaaactac tcaagaggaa gatggctgta gctgccgatt tccagaagaa | 780 |
| gaagaaggag gatgtgaact gagagtgaag ttcagcagga gcgcagacgc ccccgcgtac | 840 |
| cagcagggcc agaaccagct ctataacgag ctcaatctag gacgaagaga ggagtacgat | 900 |
| gttttggaca agagacgtgg ccgggaccct gagatggggg aaagccgag aaggaagaac | 960 |
| cctcaggaag gcctgtacaa tgaactgcag aaagataaga tggcggaggc ctacagtgag | 1020 |
| attgggatga aggcgagcg ccggaggggc aaggggcacg atggccttta ccagggtctc | 1080 |
| agtacagcca ccaaggacac ctacgacgcc cttcacatgc aggccctgcc ccctcgctaa | 1140 |

<210> SEQ ID NO 37
<211> LENGTH: 1154
<212> TYPE: DNA
<213> ORGANISM: Artificial Sequence
<220> FEATURE:
<223> OTHER INFORMATION: Nucleotide sequence of CRL5

<400> SEQUENCE: 37

| | |
|---|---|
| atggccttac cagtgaccgc cttgctcctg ccgctggcct tgctgctcca cgccgccagg | 60 |
| ccggccccaa tgacacagac aaccccactg aaaacctctt gggtgaactg cagcaatatg | 120 |
| atcgacgaga tcatcacaca cctgaagcag cccctctgc ccctgctgga tttcaacaat | 180 |
| ctgaacggcg aggaccagga tatcctgatg gagaacaatc tgagacggcc caacctggag | 240 |
| gcctttaatc gggccgtgaa gagcctgcag aacgccagcg ccatcgagtc catcctgaag | 300 |
| aatctgctgc catgtctgcc actggcaacc gcagcaccta caaggcaccc aatccacatc | 360 |
| aaggacggcg attggaatga gttcaggcgc aagctgacct tttacctgaa aacactggaa | 420 |
| aacgctcagg cacagcagac cacactgtca ctggcaatct tcactagtac cacgacgcca | 480 |
| gcgccgcgac caccaacacc ggcgcccacc atcgcgtcgc agcccctgtc cctgcgccca | 540 |
| gaggcgtgcc ggccagcggc gggggcgca gtgcacacga gggggctgga cttcgcctgt | 600 |
| gatatctaca tctgggcgcc cttggccggg acttgtgggg tccttctcct gtcactggtt | 660 |
| atcacccttt actgcccttt attattttct gggtgaggag taagaggagc aggctcctgc | 720 |
| acagtgacta catgaacatg actccccgcc gccccgggcc cacccgcaag cattaccagc | 780 |
| cctatgcccc accacgcgac ttcgcagcct atcgctccag agtgaagttc agcaggagcg | 840 |
| cagacgcccc cgcgtaccag cagggccaga accagctcta taacgagctc aatctaggac | 900 |
| gaagagagga gtacgatgtt ttggacaaga gacgtggccg ggaccctgag atgggggaa | 960 |
| agccgagaag gaagaaccct caggaaggcc tgtacaatga actgcagaaa gataagatgg | 1020 |
| cggaggccta cagtgagatt gggatgaaag gcgagcgccg gaggggcaag gggcacgatg | 1080 |
| gcctttacca gggtctcagt acagccacca aggacaccta cgacgccctt cacatgcagg | 1140 |
| ccctgccccc tcgc | 1154 |

<210> SEQ ID NO 38
<211> LENGTH: 1283
<212> TYPE: DNA
<213> ORGANISM: Artificial Sequence
<220> FEATURE:
<223> OTHER INFORMATION: Nucleotide sequence of CRL6

<400> SEQUENCE: 38

| | |
|---|---|
| atggccttac cagtgaccgc cttgctcctg ccgctggcct tgctgctcca cgccgccagg | 60 |
| ccggccccaa tgacacagac aaccccactg aaaacctctt gggtgaactg cagcaatatg | 120 |
| atcgacgaga tcatcacaca cctgaagcag cccctctgc ccctgctgga tttcaacaat | 180 |

```
ctgaacggcg aggaccagga tatcctgatg gagaacaatc tgagacggcc caacctggag    240
gcctttaatc gggccgtgaa gagcctgcag aacgccagcg ccatcgagtc catcctgaag    300
aatctgctgc catgtctgcc actggcaacc gcagcaccta caaggcaccc aatccacatc    360
aaggacggcg attggaatga gttcaggcgc aagctgacct tttacctgaa acactggaa     420 aacgctcagg cacagcagac cacactgtca ctggcaatct tcactagtac cacgacgcca    480
gcgccgcgac caccaacacc ggcgcccacc atcgcgtcgc agcccctgtc cctgcgccca    540
gaggcgtgcc ggccagcggc ggggggcgca gtgcacacga ggggctgga cttcgcctgt     600 gatatctaca tctgggcgcc cttggccggg acttgtgggg tccttctcct gtcactggtt    660
atcacccttt actgcccttt attattttct gggtgaggag taagaggagc aggctcctgc    720
acagtgacta catgaacatg actccccgcc gccccgggcc cacccgcaag cattaccagc    780
cctatgcccc accacgcgac ttcgcagcct atcgctccaa acggggcaga agaaactcc     840 tgtatatatt caaacaacca tttatgagac cagtacaaac tactcaagag gaagatggct    900
gtagctgccg atttccagaa gaagaagaag gaggatgtga actgagagtg aagttcagca    960
ggagcgcaga cgccccgcg taccagcagg ccagaaccca gctctataac gagctcaatc     1020
taggacgaag agaggagtac gatgttttgg acaagagacg tggccgggac cctgagatgg    1080
ggggaaagcc gagaaggaag aaccctcagg aaggcctgta caatgaactg cagaaagata    1140
agatggcgga ggcctacagt gagattggga tgaaaggcga cgccggagg ggcaaggggc     1200 acgatggcct ttaccagggt ctcagtacag ccaccaagga cacctacgac gcccttcaca    1260
tgcaggccct gcccccctcgc taa                                            1283

<210> SEQ ID NO 39
<211> LENGTH: 456
<212> TYPE: DNA
<213> ORGANISM: Artificial Sequence
<220> FEATURE:
<223> OTHER INFORMATION: IL-3 nucleotide sequence after the codon
      optimization

<400> SEQUENCE: 39
atgagtagac tgcccgtgct gctgctgctg cagctgctgg tgcgacctgg actgcaggcc     60
ccaatgacac agacaacccc actgaaaacc tcttgggtga actgcagcaa tatgatcgac    120
gagatcatca cacacctgaa gcagcccct ctgcccctgc tggatttcaa caatctgaac     180
ggcgaggacc aggatatcct gatggagaac aatctgagac ggcccaacct ggaggccttt    240
aatcgggccg tgaagagcct gcagaacgcc agcgccatcg agtccatcct gaagaatctg    300
ctgccatgtc tgccactggc aaccgcagca cctacaaggc acccaatcca catcaaggac    360
ggcgattgga atgagttcag gcgcaagctg acctttacc tgaaaacact ggaaaacgct    420
caggcacagc agaccacact gtcactggca atcttc                              456

<210> SEQ ID NO 40
<211> LENGTH: 152
<212> TYPE: PRT
<213> ORGANISM: Artificial Sequence
<220> FEATURE:
<223> OTHER INFORMATION: IL-3 amino acid sequence
```

```
<400> SEQUENCE: 40

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
                20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
                115                 120                 125

Lys Leu Thr Phe Tyr Leu Lys Thr Leu Glu Asn Ala Gln Ala Gln Gln
        130                 135                 140

Thr Thr Leu Ser Leu Ala Ile Phe
145                 150
```